United States Patent [19]
Toback et al.

[11] Patent Number: 5,476,922
[45] Date of Patent: Dec. 19, 1995

[54] METHODS AND COMPOSITIONS FOR THE PREPARATION AND USE OF AUTOCRINE GROWTH FACTORS

[75] Inventors: F. Gary Toback, Chicago; Margaret Walsh-Reitz, River Forest, both of Ill.; Stephen L. Gluck, St. Louis, Mo.

[73] Assignee: ARCH Development Corporation, Chicago, Ill.

[21] Appl. No.: 126,103

[22] Filed: Sep. 22, 1993

Related U.S. Application Data

[63] Continuation of Ser. No. 764,689, Sep. 24, 1991, abandoned, which is a continuation-in-part of Ser. No. 66,059, Jun. 24, 1987, Pat. No. 5,135,856.

[51] Int. Cl.$^6$ .............................. C07K 2/00; C07K 14/47; C07K 14/475
[52] U.S. Cl. .................... 530/399; 530/300; 530/324; 530/414; 930/120; 424/545; 424/558; 424/574
[58] Field of Search ..................... 530/399, 324, 530/300, 414; 514/2, 12; 930/120; 424/545, 558, 574

[56] References Cited

U.S. PATENT DOCUMENTS 4,670,539  6/1987  Sirbasku et al. ..................... 530/324

OTHER PUBLICATIONS

Stryer, L. 1975, in: *Biochemistry*, W. H. Freeman and Co. San Francisco, Calif. pp. 22–30.
Cantor et al. 1980, in: *Biophysical Chemistry*, Part I. The Conformation of *Biophysical Macromolecules*, W. H. Freeman and Co. San Francisco, Calif., 54–56.
Katz & Dong, *BioTechniques*, 8(5):546–555, 1990.
*National Kidney and Urologic Diseases Advisory Board Long-Range Plan*, U.S. Department of Health and Human Services, 1990.
Kato et al., *J. Chromatog.*, 447:212–220, 1988.
Walsh–Reitz et al., *Proc. Natl. Acad. Sci.*, 83:4764–4768, 1986.
Sporn & Roberts, *Nature*, 313:745–747, 1985.
Mordan & Toback, *Am. J. Physiol.*, 246:C351–C354, 1984.
Walsh–Reitz et al., *Am. J. Physiol.*, 247:C321–C326, 1984.
Toback et al., *Am. J. Physiol.*, 247:C14–C19, 1984.
Moolenaar et al., *Cell*, 23:789–798, 1981.
Holley et al., *Proc. Natl. Acad. Sci.*, 77(10):5989–5992, 1980.
Toback, *Kidney International*, 12:193–198, 1977.
Toback et al., *Am. J. Physiol.*, 232(2):E216–E222, 1977.

*Primary Examiner*—Christopher S. F. Low
*Attorney, Agent, or Firm*—Foley & Lardner

[57] ABSTRACT

Autocrine growth factors and isoforms of those factors have been identified, isolated, purified and manipulated. Nucleic acid segments coding for the factors, and antibodies directed to the factors are also aspects of the present invention. The effect of these growth factors on cells is to enhance their growth by increasing mitogenesis. In particular, the growth factors stimulate kidney epithelial cell growth. The growth factors differ from others previously reported in their molecular weights and other properties, for example, resistance to denaturation by dithiothreitol. Methods of preparation and use of the factors are also described. The growth factors are released from kidney epithelial cells by short exposures to a low-sodium environment. The factors have potential for treatment of kidney disease.

1 Claim, 21 Drawing Sheets

DURATION OF EXPOSURE
TO LOW-Na$^+$ MEDIUM

APPEARANCE OF GROWTH-
PROMOTING ACTIVITY
IN CONDITIONED MEDIUM

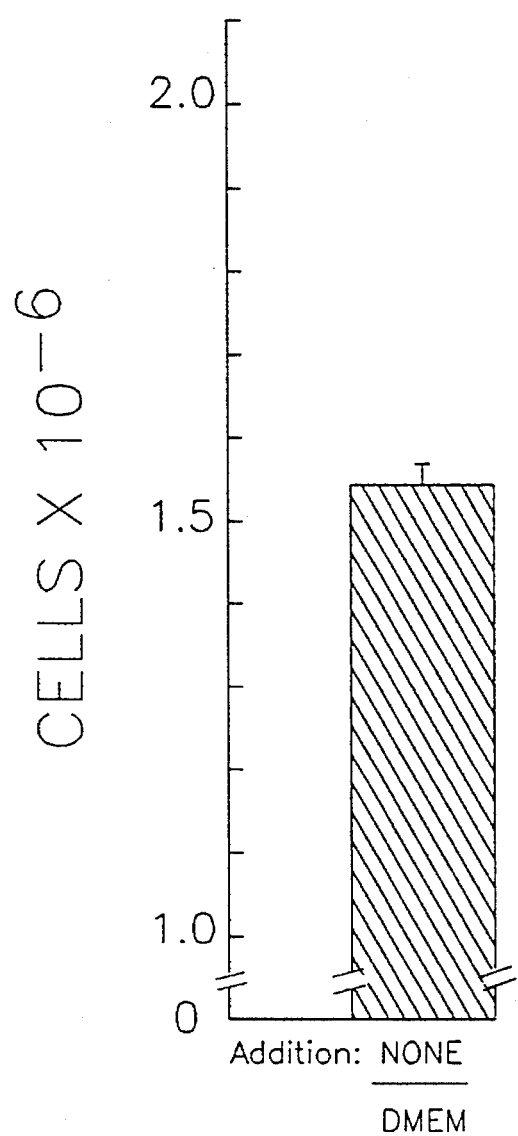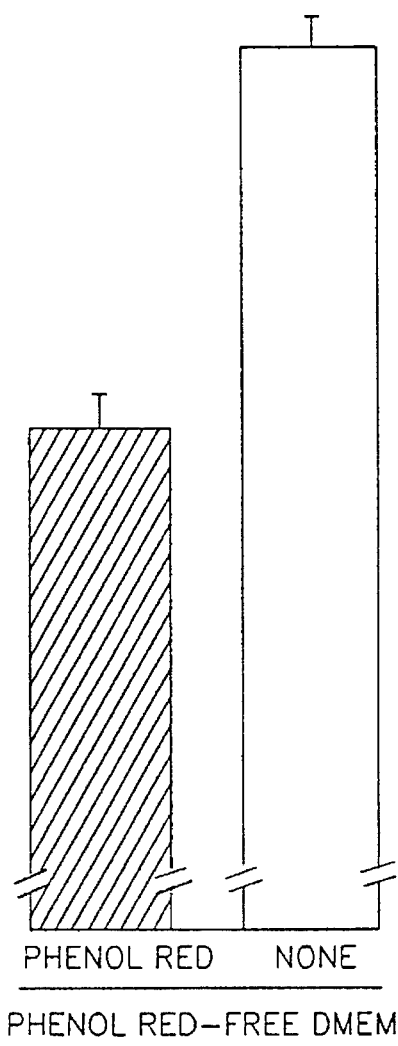

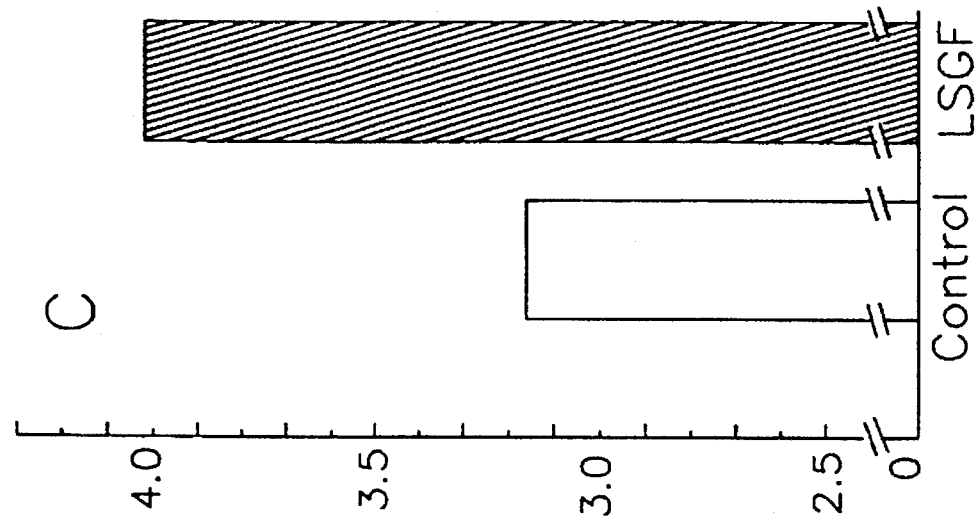
FIG. 13A  FIG. 13B  FIG. 13C
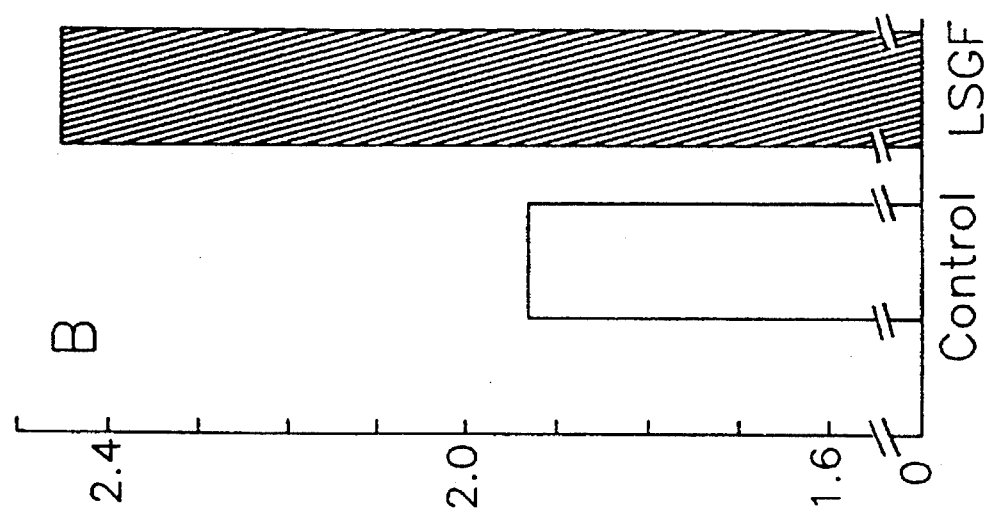
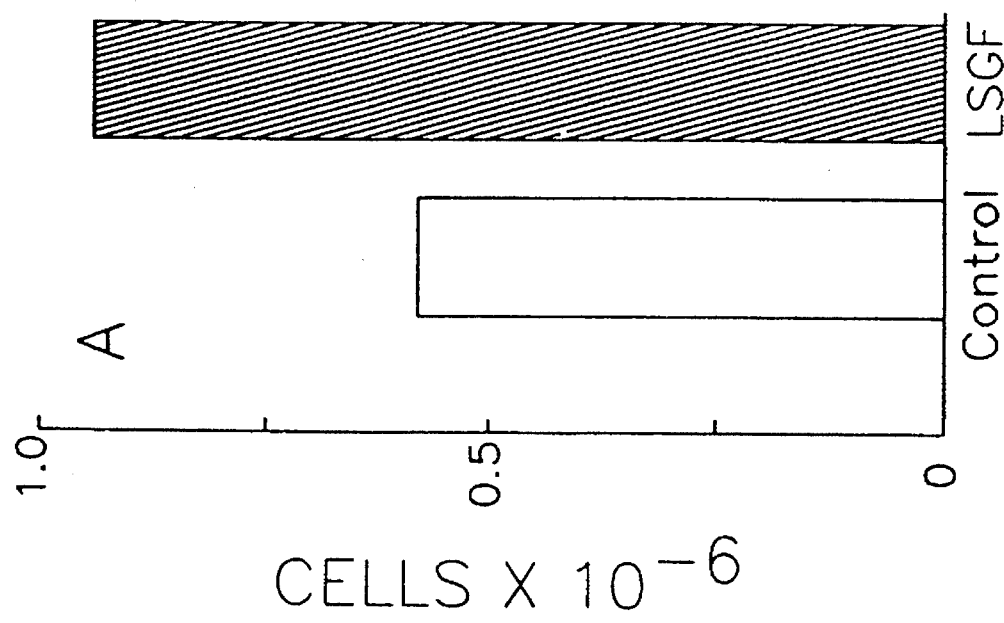

METHODS AND COMPOSITIONS FOR THE PREPARATION AND USE OF AUTOCRINE GROWTH FACTORS

The government may own certain rights to the present invention pursuant to grants from USPHS AM 34788, AM 18413, GM 22328, and DK 39689. This is a continuation of 07/764,689 filed Sep. 24, 1991, now abandoned, which is a continuation-in-part application of 07/066,059 filed on Jun. 24, 1987, now U.S. Pat. No. 5,135,856.

BACKGROUND OF THE INVENTION

1. Field of the Invention

The present invention relates to the identification, isolation and purification of autocrine growth factors, and to nucleic acid segments coding for the growth factors. The present invention also relates to methods of preparing the factors, including recombinant genetic technology, and to use of the growth factors to enhance cell growth, in particular, renal epithelial cell growth. Cellular growth enhancement is useful in treating kidney disease.

2. Description of the Related Art a. Kidney Disease is a Major Public Health Problem

Acute renal failure refers to the abrupt disruption of previously normal kidney function. This serious clinical condition is due to a wide variety of mechanisms including circulatory failure (shock), vascular blockage, glomerulonephritis, and obstruction to urine flow. Acute renal failure frequently arises as a complication of abdominal or vascular surgery. Also, due to continued improvements in prenatal care, low birth weight, high-risk neonates may now survive lung and heart problems, only to die from complications of acute renal failure caused by infection or drug toxicity. Of particular clinical importance are cases of acute renal failure associated with trauma, sepsis, postoperative complications, or medication, particularly antibiotics. (National Center for Health Statistics, 1985, Table 1, National Institute of Health, 1990).

Population data from the United States in 1985 further illustrate the nature of the problem. Acute renal failure was cited as a contributing cause in 26,922 deaths. The condition affects people of all ages, but those 65 years and older are almost five times more likely to be hospitalized for acute renal failure than those ages 45 to 64. Nearly two-thirds of all hospitalizations for acute renal failure occur in persons 65 years and older. Of those in that age group, black Americans were nearly twice as likely as white Americans to be hospitalized for acute renal failure. Acute renal failure is the most costly kidney or urologic condition requiring hospitalization. In 1985 there were 139,134 hospitalizations for the disease at a cost of $1.3 billion, or $9,329 per hospital discharge.

In recent years there has been an increase in cases of acute renal failure, which can be attributed in part to medical progress. Most cases today result from the ability to perform complicated surgery in older patients, which can lead to post-operative complications, and the use of complex drugs such as antibiotics that successfully overcome previously fatal diseases. Unfortunately, these same drugs can be toxic to the kidneys, particularly in elderly persons. Because of the increasing age of the hospital population and advances in complicated medical and surgical techniques, cases of acute renal failure are expected to increase still more in number and significance unless significant advances in treatment modalities are made.

b. Treatment Modalities for Kidney Disease are Inadequate

Some advances have been made in understanding the pathophysiology of acute renal failure, including the toxicity of drugs to the kidney and the effects of oxygen deficit and reintroduction. Current treatment of the disorder depends on recognition of the underlying causes. Rapid fluid resuscitation of trauma and burn victims undoubtedly has prevented some cases. Carefully monitored administration of nephrotoxic drugs also has the potential to reduce the incidence of acute renal failure.

Dialysis may be required to prevent death due to accumulating waste products or from fluid overload or chemical imbalance. Despite some advances, the mortality rate associated with kidney disease still has not changed in many years. These treatment modalities have focussed on preventing further deterioration rather than promoting organ repair. The latter approach would benefit from harnessing cell growth and repair processes.

c. Growth Factors to Harness Cell Growth and Repair Processes

Growth factors produced by cultured cells have been identified which, when present in tissue culture medium, will enhance the rate of division of normal, untransformed cells. Identification, isolation and purification of autocrine growth factors, that is, factors produced by a specific cell which are capable of regulating that cell's growth and division, would have important clinical applications. Certain cells might be targeted for growth enhancement by use of specific factors without disrupting the growth rates of other types of cells.

Mitchell et al. (1977), Roberts et al. (1981), and Stoker et al. (1971) isolated growth stimulating proteins from animal cells and transformed cells. Transformed cells are abnormal cells which are no longer responsive to temporal and behavioral growth limits on normal cells. There is an association between transformed and malignant cancer cells.

In other reports, factors were merely suspected by observing cell behavior. Mordan and Toback (1984) attempted to determine why accelerated kidney growth was observed empirically by several investigators, when potassium (K) was relatively low. The hypothesis explored was that cell growth was subject to autocrine control. These authors developed an in vitro model to identify factors that mediate renal growth. Molecules of an apparent molecular weight greater than 12–14 kD and less than 30 kD were separated during dialysis of medium conditioned by cells while exposed to a concentration of potassium that was lower (3.2 mM) than control (5.4 mM). Aliquots of this dialysate were tested for their effect on cell proliferation. The effects of a previously reported growth inhibitor were also tested. However, the factors that stimulated growth in $K^+$ deficient animals were neither identified nor isolated.

Some growth enhancers and inhibitors were associated with transformed cells which cannot be assumed to be the same as those that control normal cells, because growth of transformed cells, many of which are malignant, is aberrant by definition. Sporn and Roberts (1985) speculated that abnormally growing cells such as transformed or malignant cells may owe their enhanced growth abilities to a growth factor. These authors hypothesized that proliferation of transformed fibroblasts is under autocrine control and that autocrine secretion occurred in cancer cells. The role of oncogenes in growth was also addressed by these authors. In discussing their hypothesis, growth factors referred to included some previously reported, transforming growth factor-type alpha (TGF-α), TGF-β, platelet-derived growth factor (PDGF), and bombesin.

The rapid stimulation by serum of electrical and ionic membrane properties of cells, and the relationship of these effects to the initiation of DNA synthesis and cell division were investigated in neuroblastoma cells (derived from malignant tissue). This stimulation was observed to be accompanied by sodium influx. However, "A crucial but unresolved question in the study of growth control concerns the molecular mechanisms by which growth factors exert their mitogenic effect." (Moolenaar et al., 1981, p. 789.)

On the negative side of cell growth control, Holley et al. (1980) isolated two high molecular weight growth inhibitors that reversibly arrested the growth of BSC-1 cells (non transformed epithelial cells of African green monkey kidney) in the $G_1$ phase of the cell cycle. Medium conditioned by crowded BSC-1 cell cultures was said to contain several growth inhibitors. A "cryptic" growth factor activated by shaking or heating was suspected but not identified. No characteristics specific to a growth factor were presented. The authors summarized their findings as follows: "The results presented here demonstrated that extremely active growth inhibitors can be recovered from the culture medium of BSC-1 cells." p. 5992. The mechanism of inhibition was not identified, and could potentially be at any of a large number of steps in cell division. Furthermore, assuming these inhibitors would act to oppose as yet unidentified growth stimulatory factors, would be merely speculation.

Several determinants of growth regulation have been identified which affect BSC-1 cells (Holley et al., 1977, 1978 a, b). These include growth factors and hormones generally present in normal serum and their receptors on the cell surface. Specific growth-stimulatory molecules contained in serum include vasopressin, glucagon, and epidermal growth factor (EGF) (Walsh-Reitz and Toback, 1983).

The growth of BSC-1 cells in culture also appears to be regulated by the cellular production of several inhibitors. These include lactate, ammonium ion, and a secreted protein which has an $M_r$ of 24,000 (Holley et al., 1978). This inhibitor protein, which has been identified as transforming growth factor (TGF)-β2, is active at very low concentrations (1 ng/ml) on epithelial cells grown in culture, impedes exit of cells from the $G_0/G_1$ (resting) phase of the cell cycle, and can be overcome by the stimulatory action of serum or EGF (Holley et al., 1978; Tucker et al., 1984; Hanks et al., 1988). This inhibitor protein appears to exert its growth inhibitory effect by interfering with cell sodium Na flux (Walsh-Reitz et al., 1984).

Although the substratum upon which cells grow in culture is often considered a critical determinant of replication and differentiation (Martin et al, 1983; Rabito et al., 1980; Gospodarowicz et al., 1984), the contribution of collagen, fibronectin and other extracellular factors to the growth of BSC-1 cells has not yet been defined in detail.

d. The Roles of Growth Factors in Growth and Repair of the Urological System Have Not Been Established Whereas no growth factor specific to kidney tissue has been previously described, several factors initially described in other types of cells have also been identified in kidney tissue or have been shown to have actions on renal cells in culture. Growth factors isolated from kidney tissue include EGF, TGF-α and β, platelet-derived growth factor (PDGF), insulin-like growth factors (IGF)-I and II, acidic and basic fibroblast growth factors (FGF), and interleukin-1 (Mendley and Toback, 1989). EGF is found in abundance in urine and renal cyst fluid (Gattone et al., 1990), and its precursor protein, preproEGF, is made by cells of the distal nephron in the mouse (Atkin et al., 1990). TGF-β1 has been isolated from bovine kidney (Roberts et al., 1983), and TGF-β2 has been reported to be an autocrine growth inhibitor for kidney epithelial cells in culture (Hanks et al., 1988). PDGF is produced by mesangial cells, stimulates mesangial cell contraction, and is an autocrine and paracrine mitogen for different types of renal cells (Silver et al., 1989). IGF-I and II are likely synthesized in the kidney, although their physiologic functions in the organ are unknown (Mendley and Toback, 1989). Both acidic and basic FGF are found in the kidney and may play a role in angiogenesis during renal embryonic development (Risau and Ekblom, 1986).

The metabolism and excretion of growth factors in acute and chronic renal failure have not yet been studied in detail. Although most of the factors probably act locally, their presence has also been detected in the circulation and in urine. Some may be filtered at the glomerulus or require intact tubular cells for degradation and might accumulate progressively in the extracellular fluid as glomerular and tubular function diminish. In this scenario, cells of the injured kidney could be exposed to abnormal concentrations of growth factors and subjected to nonphysiologic growth-regulatory signals (Klahr et al., 1988; Kujubu and Fine, 1989).

It was noted that renal epithelial cells responded to perturbations in the extracellular concentration of K or Na by initiating DNA synthesis (Walsh-Reitz et al., 1983, 1984, 1986).

The approach taken in the present invention is to develop methods and compositions for the repair of kidney damage by stimulating kidney cells to grow and divide. The use of growth factors capable of stimulating renal cell growth as disclosed in the present specification offers new therapeutic avenues for treatment of kidney disease, and new insights into mechanisms of kidney damage.

SUMMARY OF THE INVENTION

This invention relates to the identification, purification and manipulation of autocrine growth factors which are capable of stimulating cells to grow and the use of inhibitors of the autocrine growth factors to control cell division. The autocrine factors of the present invention are further defined as having an apparent molecular weight of approximately 3,000–10,000 daltons as determined by SDS-polyacrylamide gel electrophoresis and ultrafiltration, and relative resistance to inhibition by dithiothreitol (DTT). The present invention relates more particularly to the identification, purification and manipulation of autocrine growth factors having an apparent molecular weight of approximately 6,000–7,000 daltons as determined by purification by reversed-phase HPLC and SDS-polyacrylamide gel electrophoresis.

This invention provides a means for attacking the serious problems associated with acute renal failure and urological disease which are costing millions of dollars, resulting in time extensive lost from human lives, and causing large numbers of deaths in the United States.

The autocrine growth factors of the present invention have been derived from non-transformed cells placed in tissue culture medium having a low sodium concentration by methods which will be described in subsequent sections. Consequently, the autocrine growth factors have been designated by the term "LSGF", that is "low sodium growth factors." This designation refers to the initial method that identified these autocrine growth factors. It does not imply any mechanisms of action for the growth factors, nor does it limit the scope of the compositions of the present invention to growth factors prepared by use of low sodium concentration. Because sodium influx is an important early signal during the onset of mitogenesis in many types of cells, it was unexpected that a decrease in extracellular $Na^+$ concentration would enhance cell proliferation.

In an illustrative embodiment, the two autocrine growth factors comprise an amino acid composition as shown in Table 1. Another characteristic of this embodiment is a biological activity of up to $2.6 \times 10^6$ activity units per mg of protein (Table 2). One activity unit of biological activity has been defined as an increased cell number of ~25–30% over a period of time. The effect of the autocrine growth factors on epithelial cells in culture is to enhance their growth by stimulating the cultures. Biological activity is defined as the response of cells in culture to the addition of autocrine growth factors.

This invention is also directed to antibodies which are directed against the autocrine growth factors described in the present application, in particular to monoclonal antibodies. These antibodies, when complexed with the growth factors, provide a means of controlling cell growth by acting as inhibitors.

With regard to the apparent molecular weights of the autocrine growth factors, they fall in the range 3,000–10,000 daltons which distinguishes them from previously reported autocrine growth factors. In particular, the apparent molecular weight of these autocrine growth factors as determined by SDS-polyacrylamide gel electrophoresis is approximately 6,000–7,000. The autocrine growth factors are further characterized as having an amino acid sequence of approximately 54 amino acids. However, these ranges are flexible.

A method of preparing autocrine growth factors comprises the steps of 1) placing cells in medium containing a low-sodium concentration; 2) allowing the cells to remain in the low-sodium concentration environment until an autocrine growth factor is released; and 3) collecting the autocrine growth factor. In particular embodiments, the low-sodium concentration environment is further defined as a buffer having a sodium concentration of less than 150 millimolar and a pH range of about 6.6–8.2. In yet more specific embodiments, the sodium concentration of the buffer is further defined as about 120–130 millimolar. The method is generally accomplished by allowing the cells to remain in the low-sodium concentration environment for about 3–5 minutes, although longer times are within the scope of this invention. Determination of the times appropriate for collection of the growth factors from any particular cell type is made by simple calibrations of the time necessary to achieve a desired level of cell enhancement in terms of increased cell numbers. Cultured cells generally divide about every 24 hours, so calibration is straightforward and is not a time consuming process.

Another aspect of this invention is the coding domain in the nucleic acid segment for autocrine growth factors as defined herein, or their biologically functional equivalents. In context, the biologically functional equivalents are defined as those nucleic acid segments that, because of codon equivalency, are capable of coding for essentially the same biologically functional autocrine growth factors. Biological function is defined as stimulation of epithelial cell division. The nucleic acid segments are further defined as DNA segments.

TABLE 1

AMINO ACID COMPOSITION OF 25-MINUTE AND 23-MINUTE LSGF ISOFORMS AND FIVE OTHER POLYPEPTIDE GROWTH FACTORS[1]

| Amino Acid | Monkey LSGF | | Mouse EGF | Human TGF-α | Human Insulin | Human IGF-I | Human IGF-II |
|---|---|---|---|---|---|---|---|
| | 25-min | 23-min | | | | | |
| Asp/Asn | 5 | 3 | 4/3 | 4/1 | 0/3 | 4/1 | 3/0 |
| Glu/Gln | 7 | 16 | 2/1 | 2/2 | 4/3 | 4/2 | 6/1 |
| Cys | 1 | 1 | 6 | 6 | 6 | 6 | 6 |
| Ser | 8 | 7 | 6 | 3 | 3 | 5 | 7 |
| Gly | 10 | 9 | 6 | 3 | 4 | 7 | 5 |
| His | 1 | 1 | 1 | 5 | 2 | 0 | 0 |
| Thr | 2 | 2 | 2 | 2 | 3 | 3 | 4 |
| Ala | 3 | 3 | 0 | 4 | 1 | 6 | 5 |
| Arg | 3 | 2 | 4 | 2 | 1 | 6 | 8 |
| Pro | 2 | 2 | 2 | 2 | 1 | 5 | 3 |
| Tyr | 1 | 0 | 5 | 1 | 4 | 3 | 3 |
| Val | 2 | 2 | 2 | 5 | 4 | 3 | 4 |
| Met | 2 | 0 | 1 | 0 | 0 | 1 | 0 |
| Ile | 2 | 1 | 2 | 0 | 2 | 1 | 1 |
| Leu | 2 | 2 | 4 | 3 | 6 | 6 | 6 |
| Phe | 1 | 1 | 0 | 4 | 3 | 4 | 4 |
| Lys | 2 | 2 | 0 | 1 | 1 | 3 | 1 |
| Trp | ND | ND | 2 | 0 | 0 | 0 | 0 |
| Mr | ~6500 | ~6500 | 6045 | 5600 | 5733 | 7649 | 7471 |
| # residues | ~54 | ~54 | 53 | 50 | 51 | 70 | 67 |

Abbreviations: LSGF = low sodium growth factor; EGF = epidermal growth factor; TGF-α = transforming growth factor-type alpha; IGF insulin-like growth factor; ND = not done
[1]Savage et al. (1973) ; Derynck et al. (1984; Rinderknecht and Humbel (1978).

Methods of preparing the autocrine growth factors and of testing their growth enhancement abilities generally employ epithelial cells, in particular those derived from kidneys. Kidney cells from both the canine kidney and the African green monkey kidney cell line have been used successfully both to prepare the autocrine growth factor activity by placing cells in low-sodium concentration growth medium, as well as using the cells as an assay to test the biological activity as measured by cell growth enhancement. The observation that at least two completely different species respond in this fashion and produce the growth factors, indicates that this is a growth factor that is likely to be conserved. Other cell types likely to yield factors include pig kidney line LLC-PK$_1$, and primary cultures of diploid rabbit proximal tubular cells.

The invention also relates to amino acid receptor sequences which bind to the autocrine growth factors, and to antibodies directed to the amino acid sequences of these receptors, in particular monoclonal antibodies. This invention also relates to other inhibitors of the receptors. The inhibitors provide a negative means of controlling cell growth.

In certain applications it is useful to clone the gene coding for the autocrine growth factors of the present invention. Three different cloning strategies are within the scope of the present invention; (i) if the sequence of a 25 amino acid fragment of LSGF is obtained, the mixed oligonucleotides primed amplification of cDNA (MOPAC) procedure to generate a probe is used to screen a BSC-1 cell cDNA library in lambda gt10 (Lee et al., 1988); (ii) if a peptide sequence of less than 25 amino acids is defined, degenerate oligonucleotides are generally synthesized and used to screen a BSC-1 cDNA library in lambda gt10; or (iii) a polyclonal monospecific rabbit antiserum (prepared as described herein) raised against purified LSGF is used to screen a BSC-1 cDNA library in lambda gt11.

Nucleic acid segments comprising nucleotide sequences which correspond to segments at least 14 nucleotide bases long which are capable of hybridizing to a nucleic acid segment capable of coding for at least the growth enhancement region of the autocrine growth factors of the present invention under stringent conditions, are other aspects contemplated for the present invention. These selected segments of the nucleic acid sequence, together with appropriate promoters and enhancers, may be incorporated into plasmids and other vectors to determine the actions and interactions of their genetic regions, their expression products, and mechanisms for control over their expression. Small segments such as these may be used as probes to detect the presence of the autocrine growth factor coding regions in various species. The nucleic acid segments may also be messenger RNA sequences for the autocrine growth factors.

Nucleic acid segments may be carried in recombinant expression vectors capable of expressing the autocrine growth factors when present in a host cell. Examples of such nucleic acid segments are those derived from the coding region for the autocrine growth factors. These nucleic acid segments may be operably linked to heterologous components in various plasmids or their functional equivalents. These components may include promoters such as those capable of controlling the host cell gene expressions or their functional equivalents. The recombinant expression vectors may comprise as a promoter either a eurokaryotic or a prokaryotic promoter, and may include a polyadenylation signal at position 3' of the carboxyl terminal amino acid. The promoter may be within a transcriptional unit of the encoded protein. Examples of host cells are BHK cells, VERO cells, E. coli, or other eurokaryotic or prokaryotic cells known to those of skill in the art to permit expression of transferred vectors according the present invention.

In an illustrative embodiment, the method of preparing an autocrine growth factor includes use of a host cell into which a nucleic acid segment has been transferred. The host cell is cultured under conditions suitable for expression, and the protein is thereby expressed. The method may also include a step wherein the autocrine growth factor is isolated and purified by methods well known to those of skill in the art. The degree of purification required will depend on the application for which the protein is intended. Alternatively, the nucleic acid segment may be expressed in a cell-free system such as a rabbit lysate, or the protein encoded by the nucleic acid segment synthesized by an automated protein synthesizer.

Some of the methods of preparing autocrine growth factors make use of the nucleic acid segments described herein and their expression in selected host cells to produce the autocrine growth factors.

A method for regenerating kidney tissue comprises the following steps: 1) preparing an autocrine growth factor as disclosed herein; 2) adding a pharmacologically acceptable carrier diluent to the growth factor preparation; and 3) contacting the kidney tissue with the growth factor-carrier composition. A therapeutic amount of the composition is administered. It is contemplated that the route of delivery of this combination to the tissue could be by intravenous infusion, localized injections or implants. Alternatively, damaged kidneys could be removed, treated in vitro, and returned to the host after the kidney is repaired.

In other aspects of the present invention, inhibitors of the autocrine growth factors are disclosed. These inhibitors may be antibodies directed to the autocrine growth factors or any other inhibitors selected by the following method from a series of candidate inhibitor substances. To determine the ability of a candidate substance to inhibit the autocrine growth factor enhancing activity, autocrine growth factors are prepared and combined with the candidate inhibitor. Epithelial cells in culture are then contacted with the combination and it is determined whether there is reduced cell growth enhancement compared to that enhancement obtained by use of the composition without the inhibitor.

BRIEF DESCRIPTION OF THE DRAWINGS

FIGS. 2A–2B. Effect of phenol red-free medium (DMEM) on growth of BSC-1 cells. Dulbecco's modified Eagle's medium (DMEM) used in conventional tissue culture work contains phenol red.

FIGS. 13A–13C. Effect of purified LSGF on growth of canine kidney epithelial cells of the MDCK line.

DETAILED DESCRIPTION OF THE INVENTION

Methods for identifying, isolating, purifying, and manipulating novel autocrine growth factors which are capable of stimulating cells to divide are presented in the following sections.

Identification of Autocrine Growth Factors

The autocrine growth factors were obtained from cells in culture. In general, cells are grown in tissue culture in vitro, they are generally grown in liquid nutrient media or buffered solutions. As a result of cell metabolism, the liquid medium in which the cells are grown subsequently contains various products of cell metabolism. This medium is called "conditioned medium (CM). For the present invention, when epithelial cells were grown in medium characterized by a lower sodium concentration than the concentration generally used for optimum cell growth, the conditioned medium (CM) was found to be capable of stimulating growth of cells.

Figure 1A:
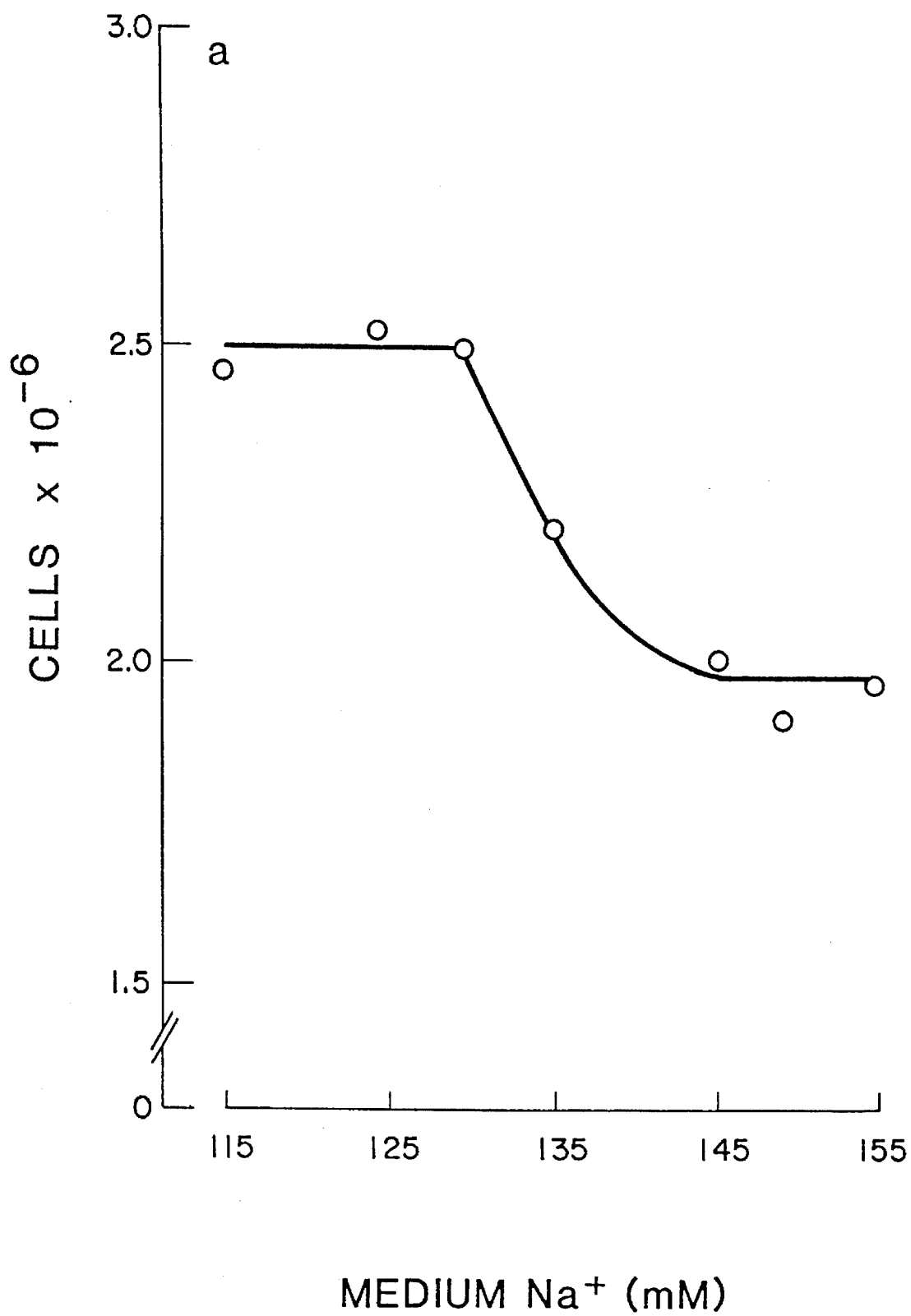
FIGS. 1A, 1B, and 1C. (a) Effect of Na$^+$ concentration in the culture medium on growth of confluent BSC-1 cells; (b) Growth of BSC-1 cells after exposure to low Na$^+$ medium for different amounts of time; (c) Appearance of growth promoting activity in low Na$^+$ medium.

The relation between sodium concentration and appearance of the growth factors was as follows. Cells were grown to a density of $10^6$ cells per 60 mm dish in medium containing 1.6 μM biotin and 1% calf serum. At time 0, this medium was aspirated, and the cells were exposed to medium containing the concentration of $Na^+$ specified on the abscissa of FIG. 1, 1.6 μM biotin, and 0.5% calf serum. Cells were counted in a hemocytometer 4 days later. When the $Na^+$ concentration of the medium was reduced, sufficient choline chloride was added so that the sum of $Na^+$ and choline concentrations was 155 mM. Cell multiplication in low $Na^+$ medium was increased compared with control (155 mM) at medium $Na^+$ concentrations of 130–115 mM ($P<0.001$). The results are shown in FIG. 1A which illustrates the effect of $Na^+$ concentration in the culture medium on growth of confluent BSC-1 cells (renal epithelial cells of the non-transformed African green monkey, *Cercopithecus aethiops*).

Figure 1B:
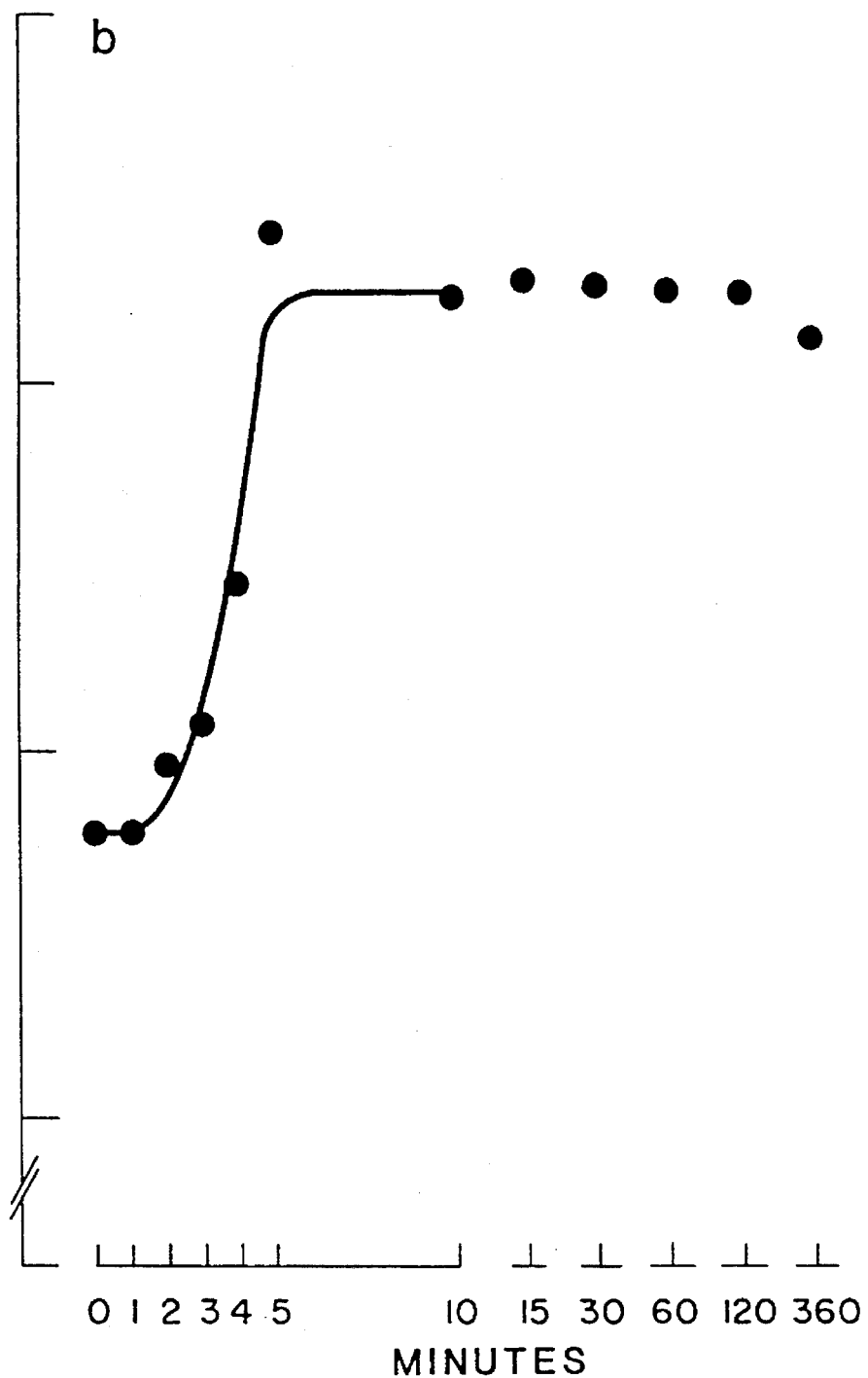

In FIG. 1B, the time cells needed to be exposed to low $Na^+$ medium to exhibit accelerated growth is presented. At time 0, cells were exposed to low $Na^+$ medium (~130 mM), and at the times specified on the abscissa, sufficient NaCl was added to raise the $Na^+$ concentration to 155 mM. Cell counts were performed on day 4. Exposure to low $Na^+$ medium for 3 ($P<0.05$) to 4 min. ($P<0.001$) was sufficient to exert a growth-stimulating effect. Results of growth of BSC-1 cells after exposure to low $Na^+$ medium for different amounts of time as shown in FIG. 1B.

Figure 1C:
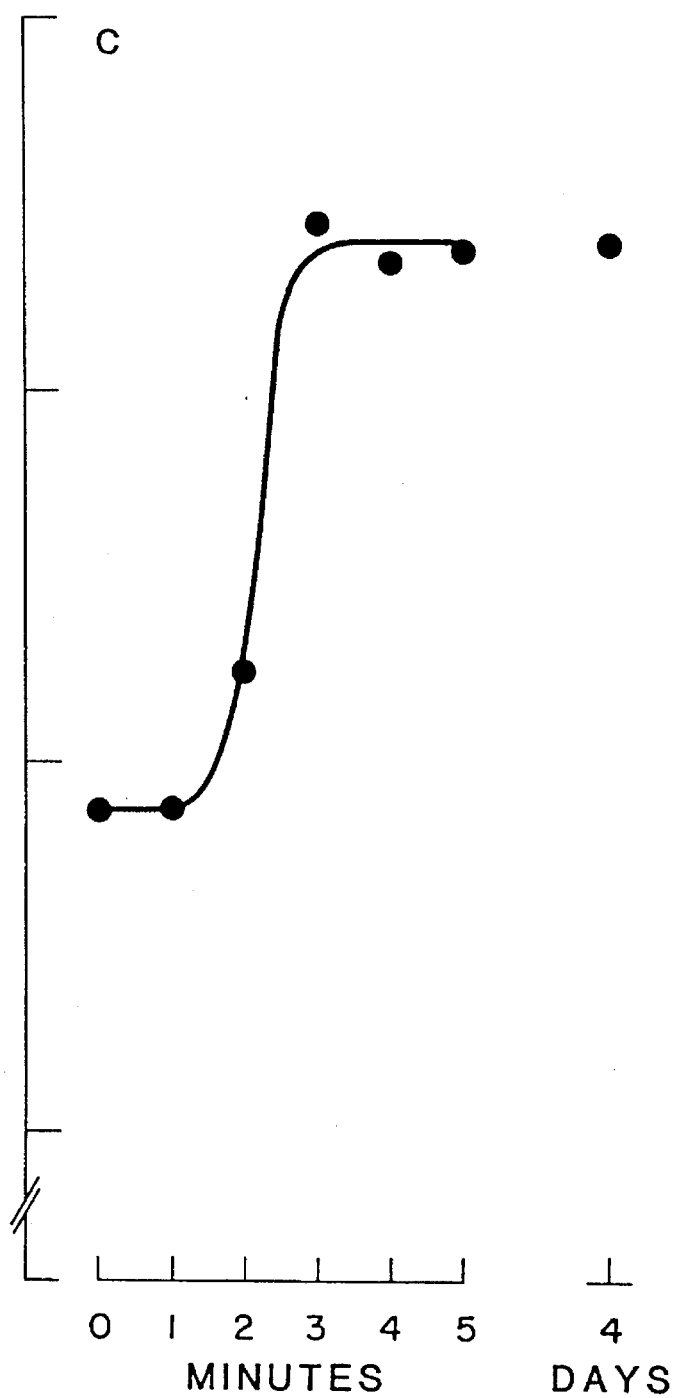

The effect of time on the appearance of growth-promoting activity in the culture medium was also determined. At time 0, low $Na^+$ medium with 0.01% serum was added to confluent cells. At the times specified on the abscissa, the CM on the dish (5 ml) was collected. $Na^+$ concentration of low $Na^+$ CM was adjusted to 155 mM by adding concentrated NaCl solution. CM was filtered and its serum concentration was raised to 0.5%. Medium on a fresh culture of BSC-1 cells was aspirated and replaced by this low $Na^+$ CM (5 ml). The number of cells per dish was determined 4 days later. Growth-promoting activity was detected in low $Na^+$ CM after 3 min. ($P<0.001$). Each value represents the mean of three to five experiments performed in triplicate; standard error was <3% of the mean (FIG. 1C).

Low-sodium autocrine growth factors were initially characterized in Dulbecco's-modified Eagle's medium (DMEM) which contains the indicator dye phenol red. Subsequent efforts designed to purify the growth factors from this medium revealed that the dye apparently bound to the growth-promoting activity from which it could be separated, but only by harsh chemical treatment. Thus in all work carried out from that point on, only phenol-red free medium was used to grow the cells and prepare conditioned medium. In this way, the growth factors do not come in contact with the dye.

The effect of phenol red-free DMEM on growth of non-transformed BSC-1 cells was determined. Cultures were grown to confluence (about $10^6$ cells/60-mm dish) in DMEM. On day 0 the medium was changed to DMEM which contains 0.04 mM phenol red, or phenol red-free DMEM to which phenol red (0.04 mM) was added, or phenol red-free medium. Biotin (1.6 μM) and calf serum (0.5%) were added to each culture, and the number of cells was counted 4 days later in a hemocytometer. Each value shown in FIGS. 2A–2B is the mean cell count ±1 standard error of the mean (SE) of 3–5 experiments performed in triplicate. As can be seen in FIGS. 2A–2B, growth was greater by 27–30% in the absence of phenol red than in its presence. Cell multiplication was similar in cultures grown in DMEM (which includes phenol red) or phenol red-free DMEM to which phenol red was added. Thus, phenol red inhibits normal growth of BSC-1 cells.

In an illustrative embodiment to prepare "LSGF", autocrine growth factors were prepared from BSC-1 cells which, hereafter will be referred to as cells, are exposed for about 5 minutes to a Tris-buffered solution (generally a pH of about 6.6 to 8.2, preferred pH 7.4) that contained approximately 130 mM NaCl and approximately 5.4 mM KCl. (As mentioned previously, another embodiment of a collecting medium is phenol-red free DMEM, however, the nutrients in DMEM are not required for release of the growth factor.) Cells appear to release the same relative amount of growth-promoting activity in the presence of the buffered salt solution as in complete DMEM. Use of a buffered salt solution eliminates exposing the cells to phenol red and the other components of DMEM which simplifies the isolation procedure because these compounds do not have to be removed in subsequent steps. The appearance of LSGF in low-Na Tris-buffer appears to be serum independent. The cells are also grown in phenol red-free DMEM so that they do not come in contact with phenol red during either growth or conditioning.

In an exemplary embodiment, an Amicon Diaflo spiral-wound membrane cartridge system was used to process pooled conditioned buffer (CB) which was ultrafiltered through a YM 10 membrane to eliminate molecules with an apparent $M_r > 10,000$, and was then ultrafiltered with diafiltration using sterile, distilled, deionized water and a YM 3 spiral filter that has a molecular weight cut off (MWCO) of 3,000. By this method 6 liters of CB can be processed to 200 ml of ultrafiltrate ($3,000 < M_r < 10,000$) within 2 days. This material was then concentrated using an Amicon pressure cell fitted with a YM 2 membrane (MWCO of 1,000) that yielded about 25 ml of concentrate which was divided into several aliquots, frozen at −70° C., and lyophilized. About 0.25 mg protein per liter of CB resulted from this part of the protocol.

Isolation and Purification Of Autocrine Growth Factors

Figure 3:
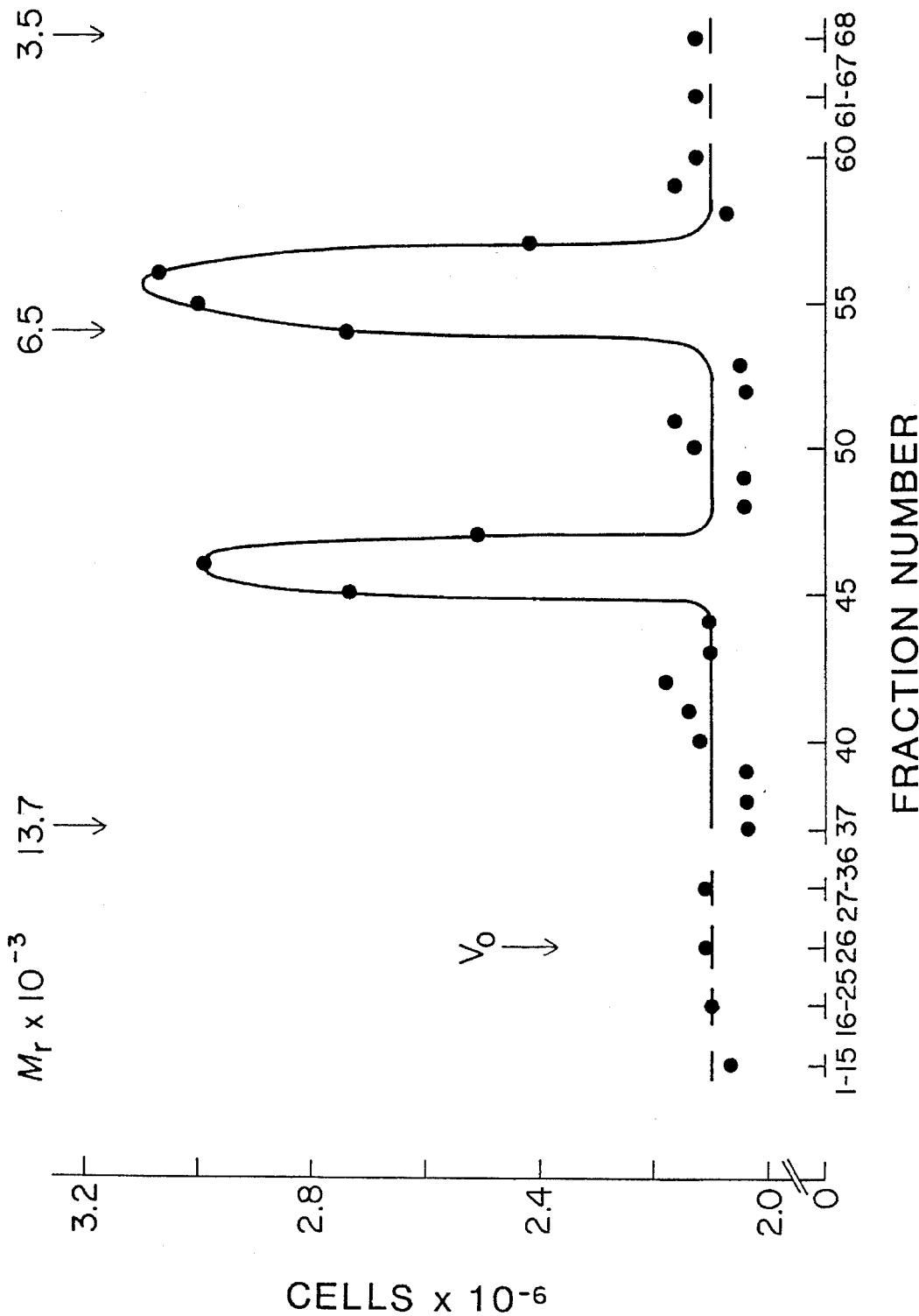
FIG. 3. Gel-filtration chromatogram of partially purified growth-promoting activity obtained from low Na$^+$ conditioned medium.

Various methods were employed to isolate and purify the autocrine growth factors identified in conditioned media, including size-exclusion chromatography and SDS-polyacrylamide electrophoresis. The preferred purification protocol utilizes ultrafiltration, diafiltration, and reversed-phase HPLC on C18 columns. A gel-filtration chromatogram of partially purified growth-promoting activity obtained from low $Na^+$ conditioned medium is shown in FIG. 3. Cultures of BSC-1 cells (60 dishes/5 ml each) were exposed to low $Na^+$ medium for 4–5 min. to prepare 300 ml of CM, which was then ultrafiltered, dialyzed, and concentrated as described. The active material with an apparent $M_r$ of >3500 and <10,000 was loaded onto a Bio-Gel P-10 column and eluted with 10 mM sodium phosphate buffer. An aliquot of each fraction was assayed for growth-stimulating activity on a culture of BSC-1 cells. Each value shown is the mean for three cultures; standard error was <3% of the mean. The column was calibrated by using protein samples of known molecular weight, as indicated by the vertical arrows (from left to right: RNase A, aprotinin, and ACTH; void volume, $V_o$, by ovalbumin). The apparent $M_r$ of the growth-stimulating activities was 6200 and 9000 daltons. The smaller protein was chosen for further purification because its potency as a mitogen was 10-fold greater than that of the larger one based on cell growth enhancement assays.

Figure 4:
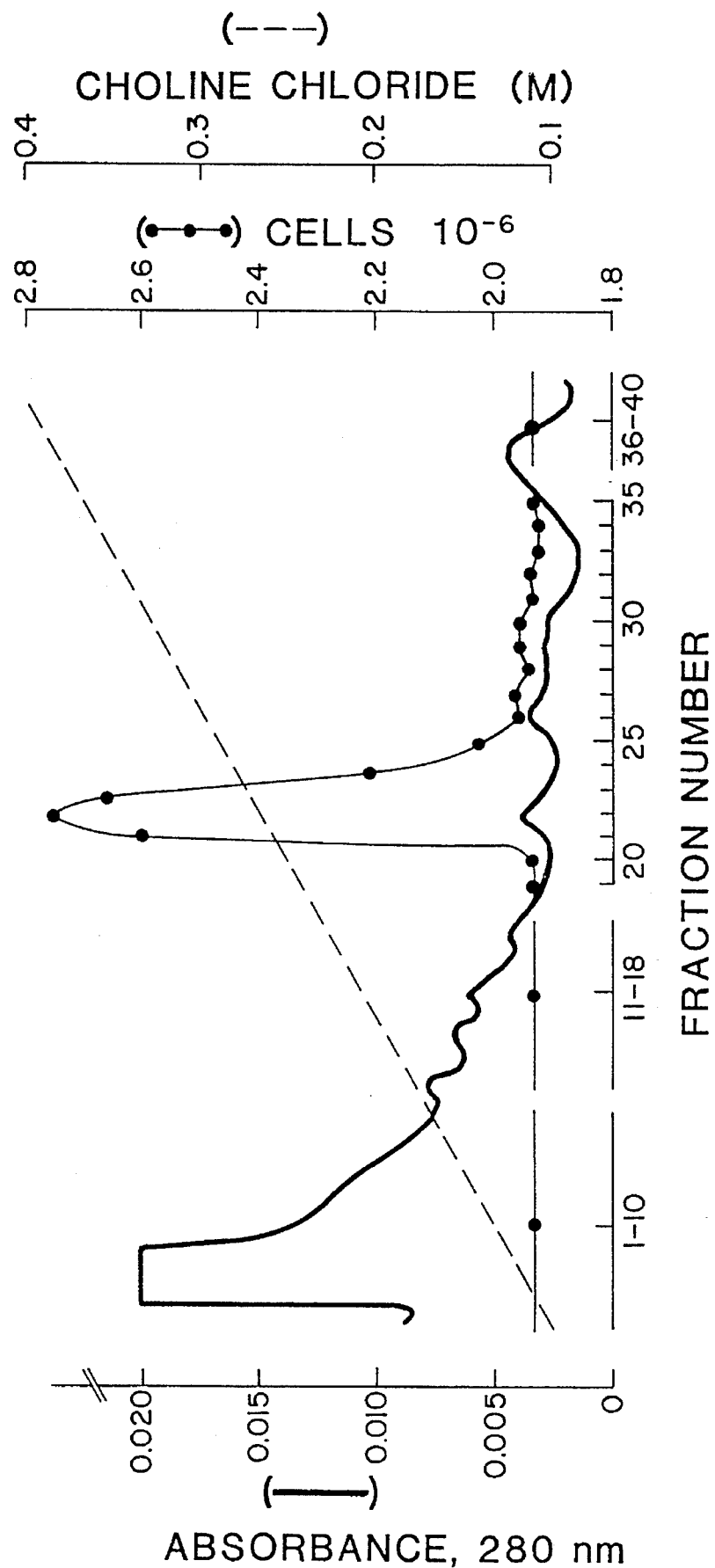
FIG. 4. High-performance anion-exchange liquid chromatography of growth-promoting activity produced by BSC-1 cells exposed to low Na$^+$ medium.

High-performance anion exchange liquid chromatography (Katz and Dong, 1990) of growth-promoting activity produced by BSC-1 cells exposed to low $Na^+$ medium was performed. Fractions 54–56 from the Bio-Gel P-10 column shown in FIG. 3 were pooled and loaded onto a Mono Q column for HPLC and eluted with a linear gradient of choline chloride (0.1–0.4M) in 10 mM sodium phosphate buffer. The thick line shows the absorbance tracing of the eluted fractions (FIG. 4). Growth-stimulating activity in each fraction (1 ml) was assayed in triplicate. The number of cells per culture is depicted on the graph as solid circles. Fractions 21–23 contained the maximum growth-promoting activity (FIG. 4).

Figure 5:
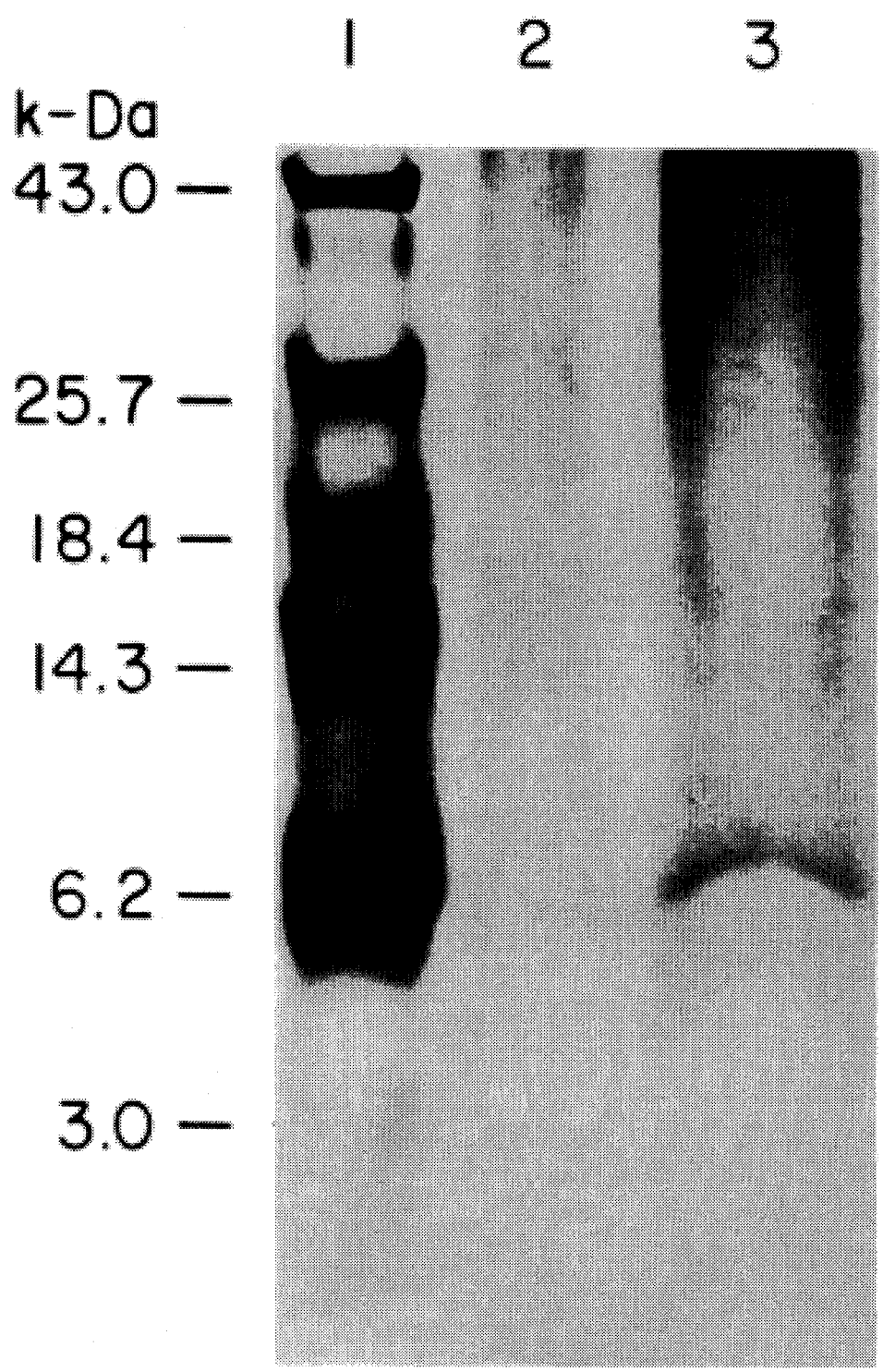
FIG. 5. NaDodSO$_4$/polyacrylamide gel electrophoresis of low Na$^+$ growth-promoting activity.

$NaDodSO_4$/polyacrylamide gel electrophoresis of low $Na^+$ growth-promoting activity was then carried out. The material in fractions 21–23 obtained as described in FIG. 4 was dialyzed, lyophilized, dissolved in sample buffer, and subjected to electrophoresis on a $NaDodSO_4$/polyacrylamide gel (15% acrylamide) containing 6M urea that was subsequently silver-stained. Proteins of known size ($M_r$, 3000–43,000) are displayed in lane 1, and sample buffer is shown in lane 2. The arrow at lane 3 indicates the growth-stimulating activity ($M_r$, 6200). Numbers on left represent $M_r \times 10^{-3}$ (FIG. 5).

To isolate and purify the autocrine growth factors from a 20-fold larger volume than described above, a concentrate prepared from 6 liters of ultrafiltered conditioned buffer is loaded onto a C18 RP HPLC column and eluted with a linear isopropanol gradient (0–50%) in 0.01M phosphoric acid. This yielded a single peak containing growth-promoting activity at ~26% isopropanol. It was found that high concentrations of residual phosphoric acid could denature the protein making it insoluble in water. This fraction was reduced in volume by vacuum centrifugation but not to dryness, collected and loaded onto a C18 RP HPLC column that was then eluted with either a linear acetonitrile gradient (0–80%) in 0.1% trifluoroacetic acid (TFA) or a linear isopropanol (0–50%) gradient in 0.1% TFA to confirm purity and remove phosphoric acid. Although this results in a very sharp single peak of protein, its biological activity, enhancement of cell growth, was lost in the presence of TFA.

Figure 6:
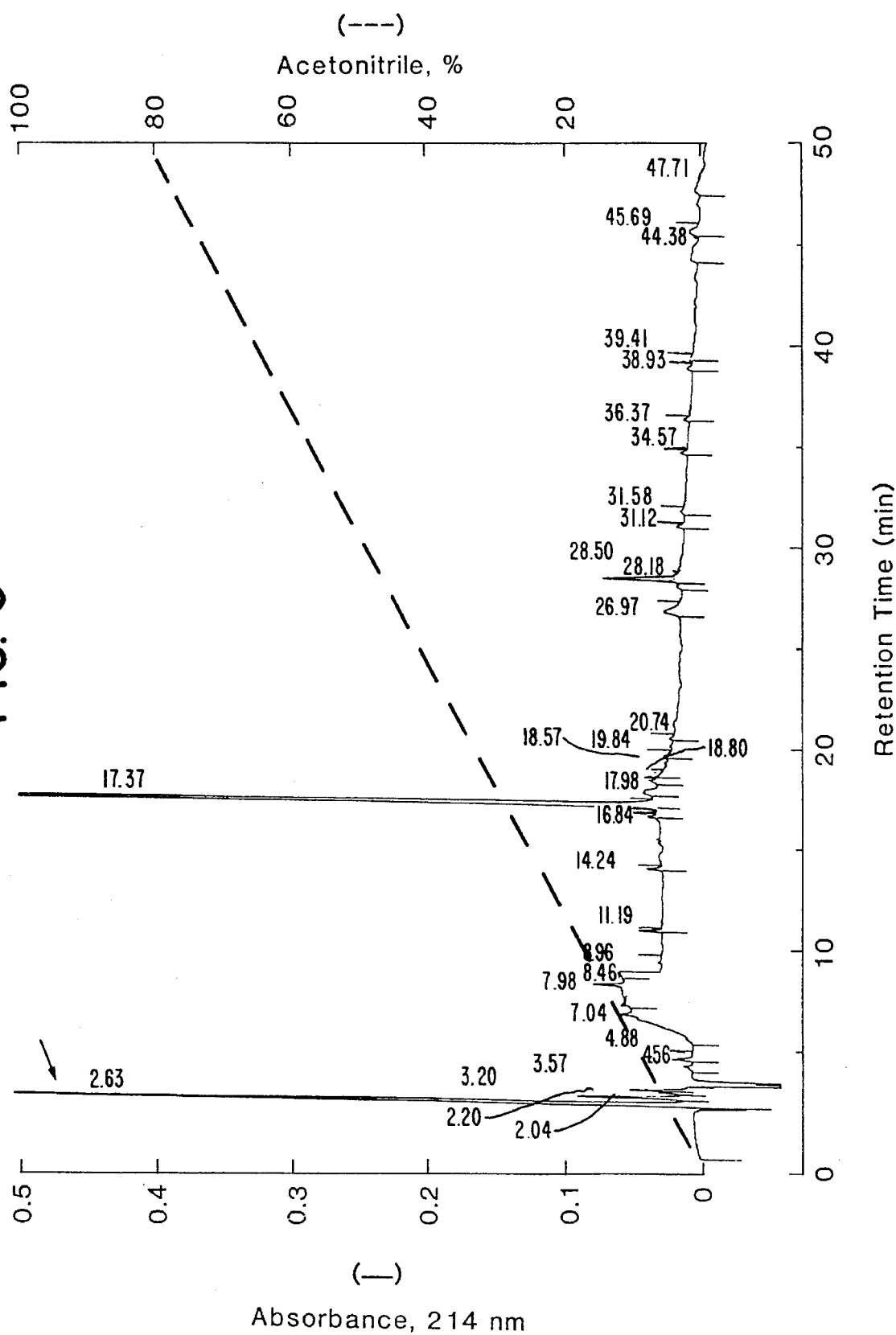
FIG. 6. High performance reversed-phase liquid chromatography (RP HPLC) of autocrine growth factors (designated LSGF).
Figure 7:
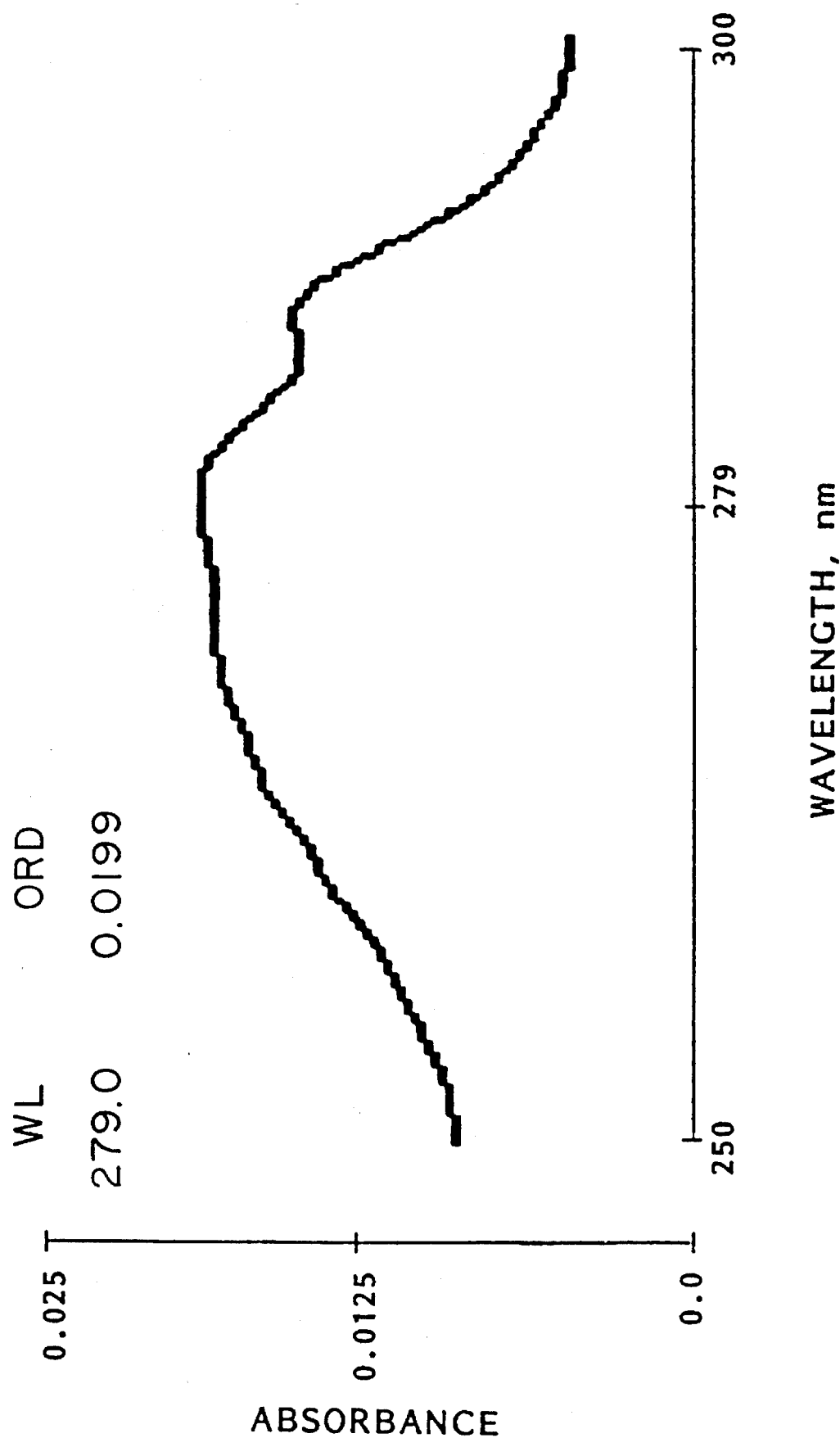
FIG. 7. Absorption spectrum of autocrine LSGF eluted from a C18 reversed-phase HPLC column by 29.6% acetonitrile/0.1% TFA.

A result of high performance reversed-phase liquid chromatography of LSGF is shown in FIG. 6. Bioactive material eluted from a C18 RP HPLC column with 26% isopropanol/0.01M phosphoric acid was loaded onto a different C18 RP HPLC column and eluted with a linear gradient of acetonitrile (0–80%) in 0.1% TFA. The solid line shows the absorbance at 214 nm of the eluted fractions. Numbers on the tracing are retention times. The peak at 29.6% acetonitrile (17.37 minutes) contains LSGF. An arrow indicates the refractive index artifact at the start of the gradient. The figure shows that a single peak was detected at 29.6% acetonitrile ($A_{214\ nm}$) which is not present in the water blank of an adjacent column fraction from the run eluted with isopropanol/phosphoric acid. An absorption spectrum was obtained on the material that appeared at 29.6% acetonitrile; its appearance was compatible with a pattern expected of a protein (FIG. 7) (WL=wavelength at maximal absorption; ORD= absorbance units on the ordinate).

The material that elutes at 26% isopropanol, has an apparent $M_r$~6,500 based on gel electrophoresis separation followed by silver staining of bands. The peak contains the largest amount of biological activity as assessed by serial dilution. It was noted that 3 or 4 other fractions that variably eluted from the column are also active. Activity in each of the ultrafiltration steps summarized in Table 2 estimates the sum of all mitogenic molecules in conditioned buffer, whereas the protein eluted at 26% isopropanol represents the predominant species.

The purification protocol described in previous paragraphs is reproducible and yields about 2 μg of LSGF protein per liter of low-Na conditioned buffer. The purified protein has been subjected to amino acid compositional analysis (Table 1) under both oxidizing and nonoxidizing conditions, and to amino acid microsequencing. The results indicate that at least in this embodiment the purified LSGF apparently have only one cysteine residue, a characteristic which is compatible with the observed resistance of its biological activity to dithiothreitol (DTT), a compound known to destroy disulfide bridges. The amino-terminus of the purified material is apparently blocked when subjected to Edman degradation and microsequencing, possibly due to the presence of a pyroglutamate residue, acetylation of the terminal amino acid (Brown et al., 1976), or other prosthetic group. Thus cleavage of the protein may be expected to obtain peptides that are suitable for microsequencing.

Isoforms of Autocrine Growth Factors

The preferred purification protocol utilizing reversed-phase high performance liquid chromatography yields isoforms of autocrine growth factors. Ultra- and diafiltered low-sodium conditioned buffer was loaded onto a C18 Brownlee column and was eluted with a linear gradient of isopropanol (0–60%) in 0.01M phosphoric acid for 1 hour. Growth-promoting activity was detected in the notched peak (FIG. 8) at ~24% isopropanol. It was noted that there were "early" and "late" portions of the notched peak. Numbers as shown on the tracing are retention times.

Figure 8:
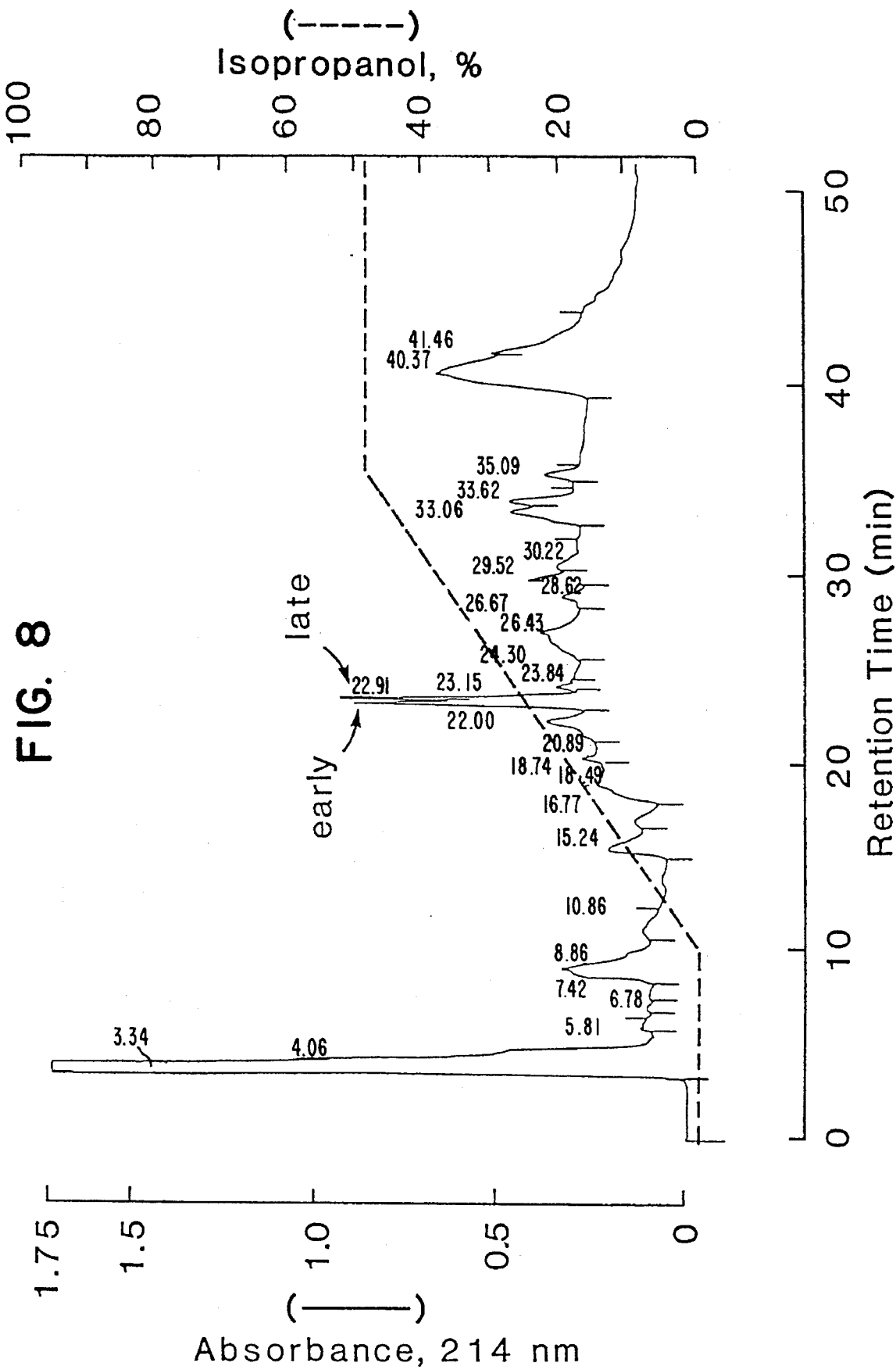
FIG. 8. High performance reversed-phase liquid chromatography of LSGF using isopropanol gradient in 0.01M phosphoric acid. Growth-promoting activity is in the notched peak at ~24% isopropanol.
Figure 9:
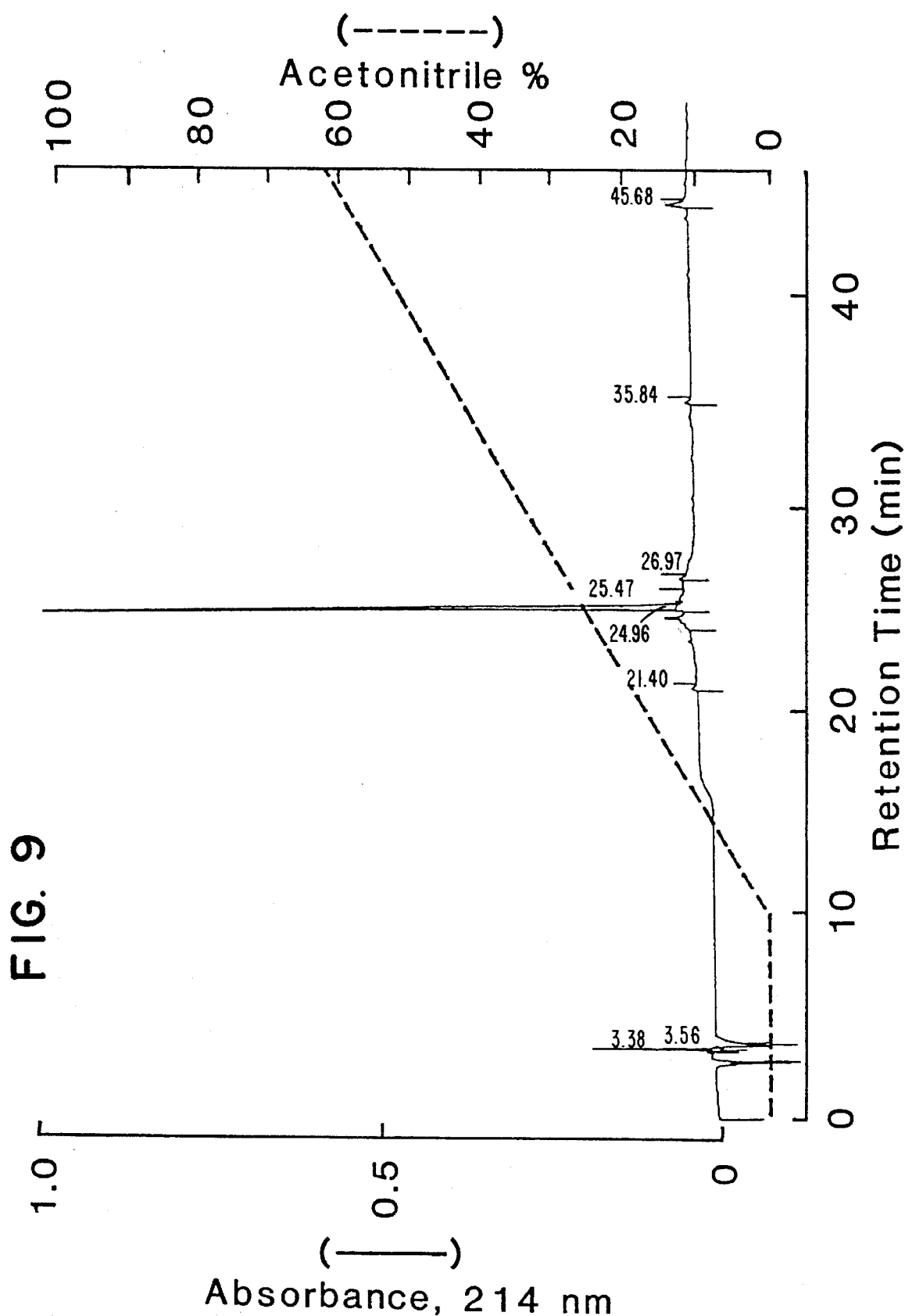
FIG. 9. Reversed-phase HPLC of LSGF; "early" portion of notched isopropanol peak shown in FIG. 8 was rechromatographed using acetonitrile gradient in 0.1% TFA. The peak represents the 25-minute isoform of LSGF.

The "early" isopropanol peak shown in FIG. 8 was manually collected and loaded onto a C18 Beckman column that was eluted with a linear gradient of acetonitrile (0–80%) in 0.1% TFA for 1 hour. Growth-promoting activity was detected at 26% acetonitrile, at an elution time of 25.47 minutes (FIG. 9). This will be referred to hereinafter as the "25-min. isoform."

Figure 10:
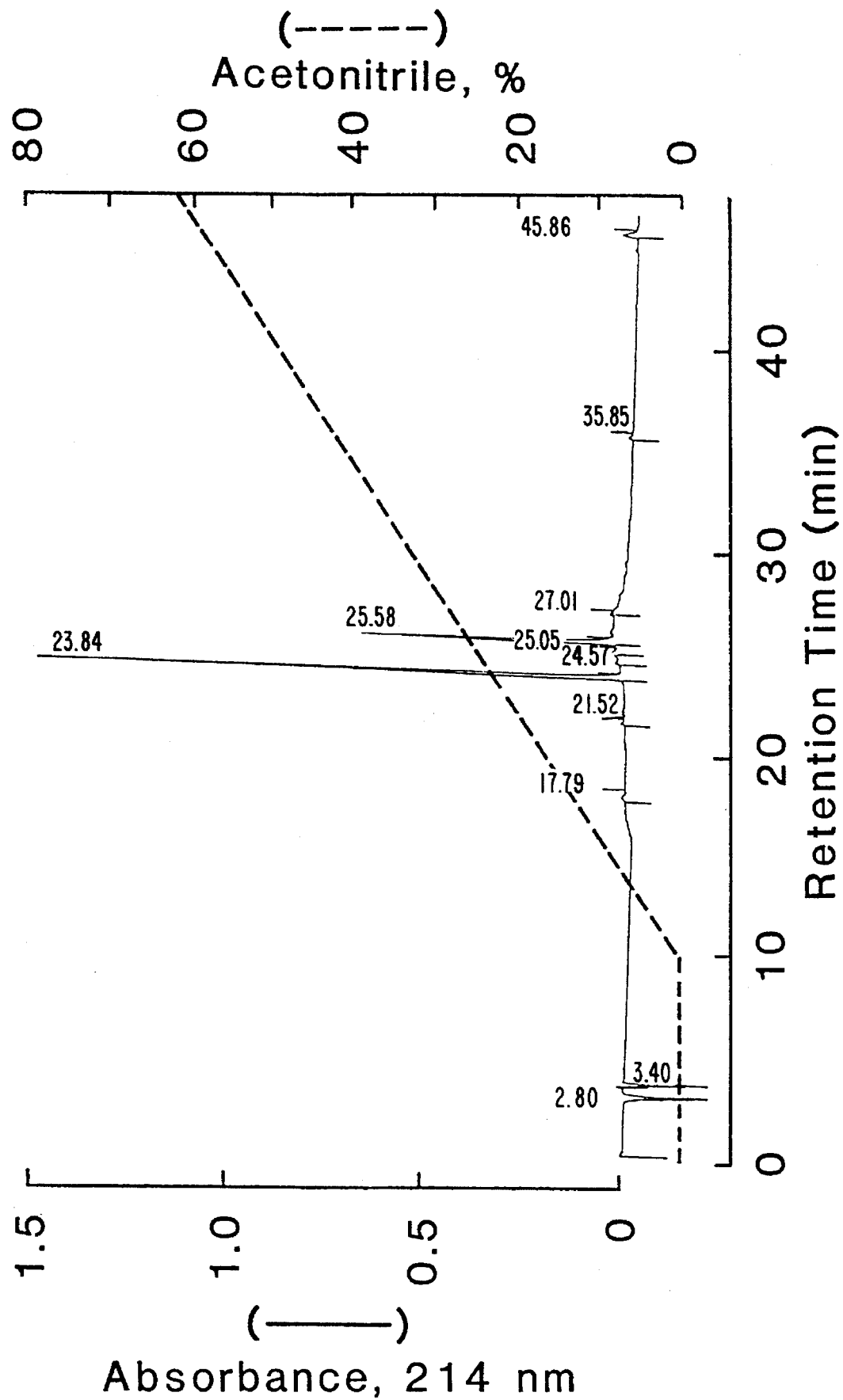
FIG. 10. Reversed phase HPLC of LSGF; "late" portion of notched isopropanol peak shown in FIG. 8 was rechromatographed using acetonitrile gradient in 0.1% TFA. The 2 peaks are the 23- and 25-minute isoforms of LSGF.

The "late" isopropanol peak was manually collected and rechromatographed as shown in FIG. 10. Bioactive material was eluted at 24% acetonitrile (elution time 23.84 min), and at 26% acetonitrile (25.50 min). The former isoform will be referred to hereinafter as the "23-min. isoform". The 23-min. material represents a new isoform, whereas the 25-min. material was previously isolated and characterized using slightly different conditions and a different gradient program as shown in FIG. 6.

The size of the two LSGF isoforms appears to be in the range of 3,000 to 10,000 daltons based on the ultrafiltration protocol used in the purification procedure. To define the size of each isoform, 3 µg of HPLC-purified protein was labeled with Na[$^{125}$I] using IODO-GEN as the iodination agent. About 350 ng of labeled materials was subjected to electrophoresis on an SDS polyacrylamide gel containing 20% acrylamide, and then an autoradiogram was prepared. In comparison to known standards, the 25-minute isoform of [$^{125}$I]LSGF migrated with an apparent $M_r$ of 6,500 as detected by autoradiography, which suggests that the molecule has at least one tyrosine residue. The 23-minute isoform was not detected by autoradiography, which suggests that it does not contain a tyrosine residue.

Several features concerning the amino acid composition of autocrine growth factors of the present invention are of interest. As shown in Table 1, the 23-minute and 25-minute isoforms appear to differ. First, as predicted from the IODO-GEN labeling experiment, the 25-minute isoform contains one tyrosine residue, whereas the 23-minute isoform does not appear to contain any. Second, the 23-minute isoform contains 16 glutamic acid/glutamine residues, whereas the 25-minute residue contains only 7, and third, the 25-minute isoform contains 2 methionine residues, where the 23-minute material has none. In general, the data confirm the conclusion reached from biological assays that both isoforms differ from known growth factors of similar size; second, the number of methionine residues in LSGF (two) is greater than that observed in the previously reported growth factors (Table 1). It is also of interest that each LSGF isoform has a single cysteine moiety, whereas each of the other 5 growth factors have 6 of them. This would account for the biological resistance of LSGF to DTT which inactivates the other growth factors listed in the table, presumably by reducing disulfide bridges formed by the cysteine residues.

TABLE 2

PURIFICATION FROM MONKEY KIDNEY EPITHELIAL CELLS
$M_r$6,000-LSGF

| Purification step Volume | protein[a] ml | Units[b] mg | Total Activity/ mg protein | Activity/ Purification | Fold |
|---|---|---|---|---|---|
| Conditioned buffer | 6,000 | 756 | 600,000 | 794 | 1 |
| Ultrafiltration | | | | | |
| $M_r$<10,000 | | 606 | 600,000 | 990 | 1.25 |
| 3,000>$M_r$ <10,000 | | 4.25 | 600,000 | $1.4 \times 10^5$ | 176 |
| 1,000>$M_r$ <10,000 | | 1.56 | 600,000 | $3.8 \times 10^5$ | 479 |
| Reversed-phase HPLC | | | | | |
| Isopropanol/phosphoric acid | | 0.0115[c] | 30,000 | $2.6 \times 10^6$ | 3,275 |
| Acetonitrile/TFA | | | * | | |

1 Activity unit = reciprocal of number ml of solution required for maximal increase in multiplication of BSC-1 cells in a confluent culture (55-mm dish) compared to control X total ml.
[a]Estimated by bicinchoninic acid (BCA) protein assay (Pierce).?
[b]There is ~30% uncertainty in these measurements which are based on serial dilutions.
[c]Estimated by amino acid compositional analysis.
*Activity lost in the presence of acetonitrile/TFA.

Renatured Autocrine Growth Factor is Active

To renature biologically inactive LSGF in acetonitrile/TFA, the solvent was removed by vacuum centrifugation, and the protein was then dissolved in water and incubated for at least 1 hour at 37° C. Growth-promoting activity of this renatured preparation was documented in cultures of BSC-1 cells. Additional studies showed that LSGF purified more than 6 months earlier could also be renatured to a fully active state by this simple approach. Both the 23-minute and 25-minute isoforms of LSGF eluted by acetonitrile/TFA were renatured by this procedure.

Mitogenic Activity of Autocrine Growth Factors

Figure 11:
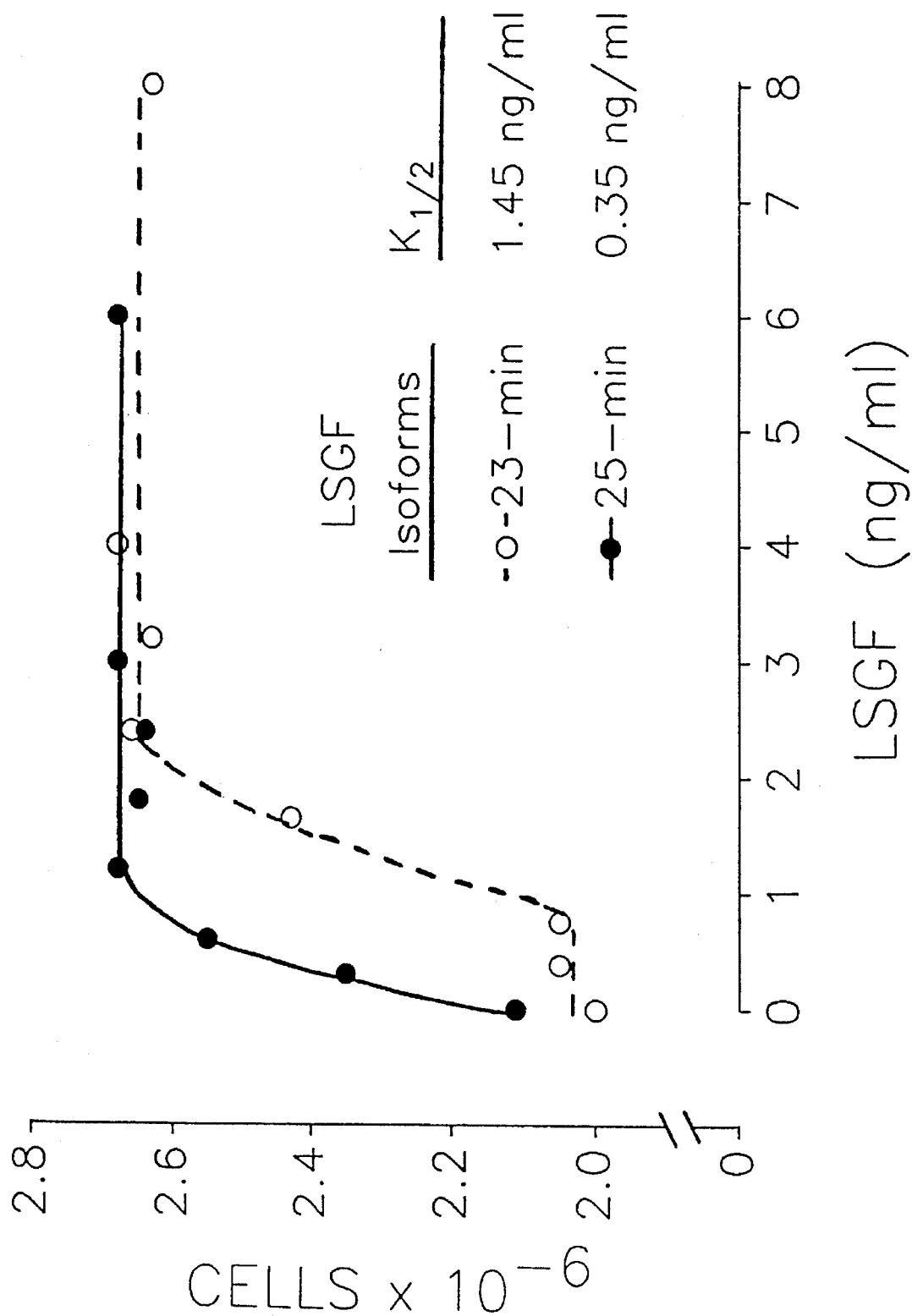
FIG. 11. Relative mitogenic potency of LSGF isoforms.

Both monkey kidney epithelial cells, of the BSC-1 line, and canine renal epithelial cells of the MDCK line, released growth-promoting activity when exposed to low-Na medium. Each of these kidney cell lines responded to addition of purified LSGF by increased mitogenic activity. Both the 23 minute and 25 minute isoforms were found to be mitogenic. (FIG. 11, 12).

Figure 12:
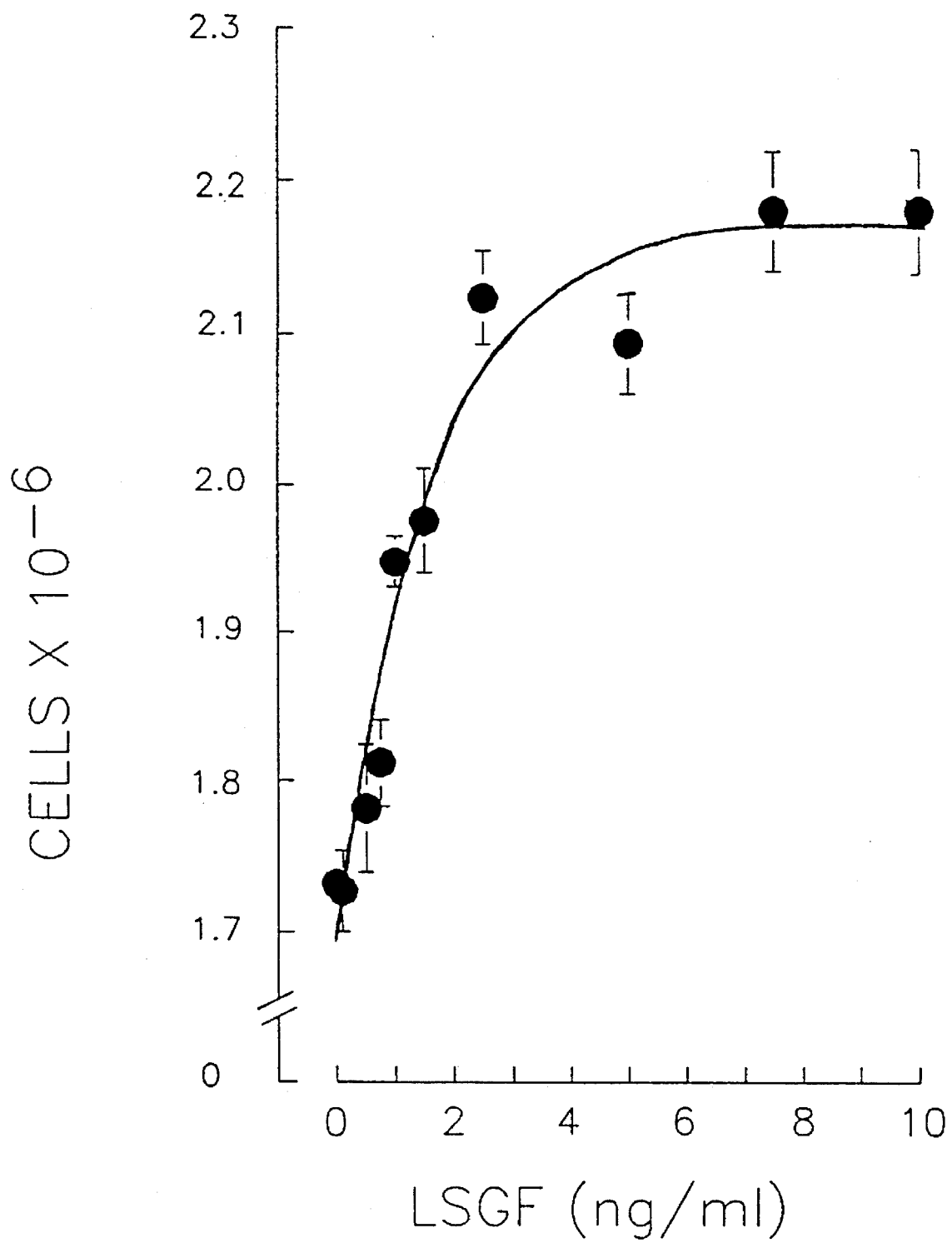
FIG. 12. Mitogenic effect of RP HPLC-purified LSGF on BSC-1 cells.

The effect of reversed-phase HPLC-purified LSGF on growth of BSC-1 cells is shown in FIG. 12. Cultures were grown to confluence (generally about $10^6$ cells/60-mm dish) in medium DMEM containing 1% calf serum. The medium was aspirated and replaced with fresh medium containing different amounts of LSGF and 0.5% serum. The number of cells was counted in a hemocytometer (a slide for counting cells which is well known to those of skill in the art) 4 days later. Two separate batches of low-sodium conditioned buffer (6 liters each) were subjected to ultrafiltration and HPLC to purify LSGF. The amount of protein isolated from each was measured by amino acid compositional analysis. Growth-promoting capacity of the 2 preparations was evaluated in separate experiments. Each value shown in FIG. 12 is the mean ±1 standard error of the mean (SE) for at least 5 cultures. The solvent used to elute LSGF from the HPLC column had no effect on cell multiplication.

The effect of purified LSGF on growth of canine kidney epithelial cells of the MDCK line is shown in FIGS. 13A–13C. Cells were plated on 60-mm plastic dishes in DMEM containing 1% calf serum and grown to different densities; panel A, $4\times10^4$/dish; panel B, $6\times10^5$; panel C, $1.2\times10^6$. Then the medium was aspirated and replaced with fresh medium containing 0.5% serum to which 5 µl of HPLC-purified LSGF (~2.5 ng protein/ml of medium) was added. The number of cells was counted in a hemocytometer 4 days later. Each value is the mean of 2 cultures; variance is <5%. The vehicle had no effect on cell multiplication. Thus, canine cells are stimulated to proliferate by purified monkey kidney LSGF protein in a cell density-independent manner.

The relative mitogenic potency of two LSGF isoforms was measured and compared. The 23- and 25-minute isoforms were purified by chromatography, and the quantity of each was measured by amino acid compositional analysis as described herein. Each LSGF isoform was renatured, diluted in water, and added to a confluent culture of BSC-1 cells grown in medium (DMEM) containing 1.6 µM biotin. The number of cells was counted 4 days later. Each value shown in FIG. 11 represents the mean of cell counts in 3 cultures. The variance was <5%. FIG. 11 shows that both isoforms of the protein are equivalent in their capacity to maximally stimulate cell multiplication, but that the 25-minute isoform appears more potent based on the 4-fold higher $K_{1/2}$ value of the 23-minute material.

Autocrine Growth Factors Are Eluted from the Extra Cellular Matrix

Figure 14:
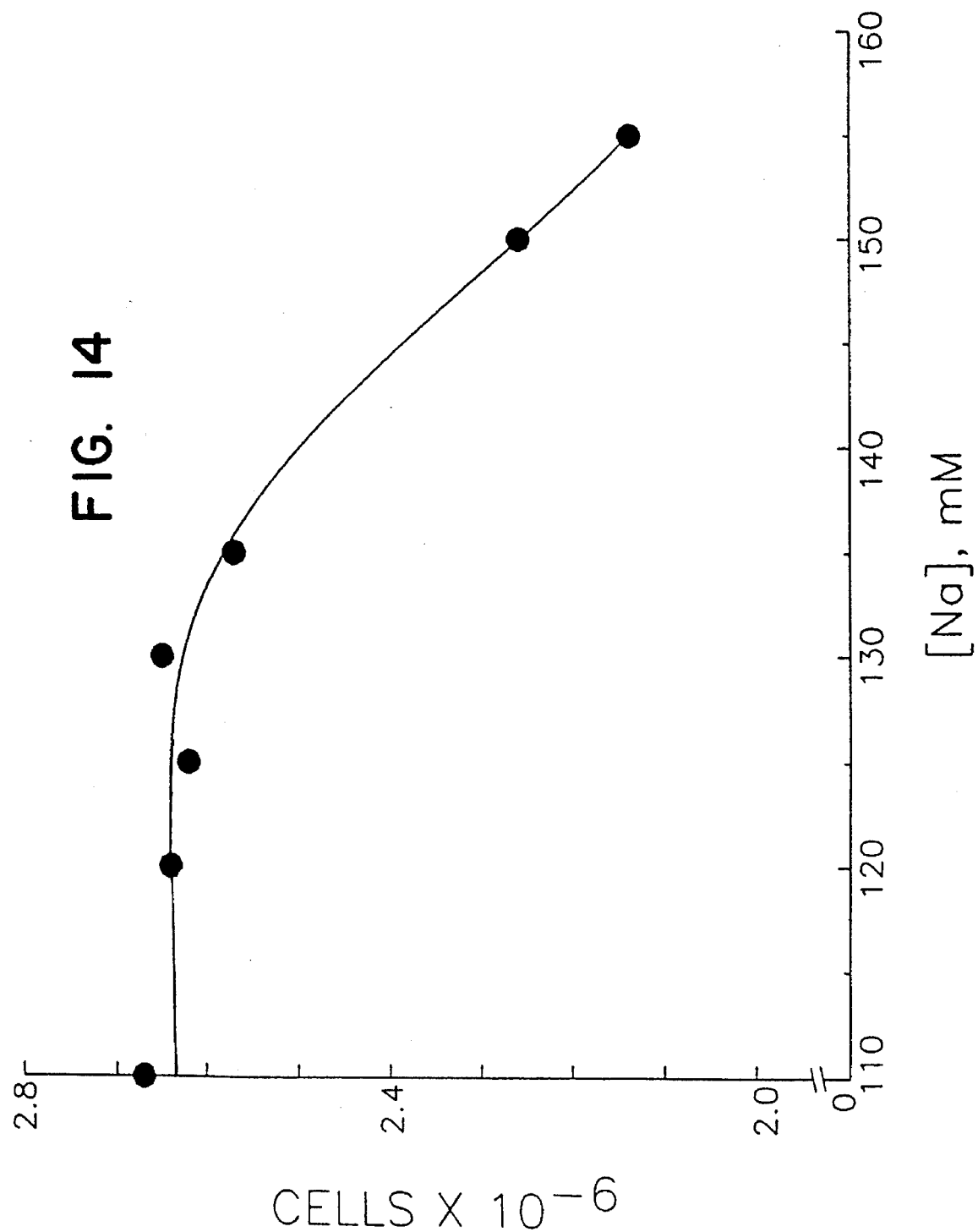
FIG. 14. Effect of Na concentration on release of growth-promoting activity from the extracellular matrix (ECM) of BSC-1 cells.

The effect of $Na^+$ concentration on release of growth-promoting activity from extracellular matrix (ECM) of BSC-1 cells is shown in FIG. 14. Cultures were grown to confluence and the cell monolayer was removed with EGTA to expose ECM that had been secreted by the cells to coat the surface of the dish. DMEM (5 ml) containing the concentration of $Na^+$ specified on the abscissa was layered onto a dish coated with ECM and incubated for 10 minutes. The solution was then removed, an aliquot (250 µl) was added to a fresh culture, and the number of cells was counted 4 days later. Each value is the mean of 4 cultures; the variance was <5%. The Na concentration of control DMEM was 155 mM.

FIG. 14 shows that addition of low-Na DMEM to dishes coated with ECM from which cells had been removed resulted in the appearance of growth-promoting activity. The profile of activity released as a consequence of progressive reduction in Na concentration was strikingly similar to that observed in the presence of cells (Walsh-Reitz et al., 1986). Subsequent studies showed that the quantity of activity released from ECM as measured by serial dilution of the low-$Na^+$ conditioned medium was also similar to that when cells were present; maximal activity was detected at dilutions of $\frac{1}{100}$ to $\frac{1}{200}$ in each instance. Additional experiments revealed that solutions of phosphate-buffered saline (PBS) containing reduced concentrations of $Na^+$ also resulted in the release of growth-promoting activity with a similar profile.

Figure 15:
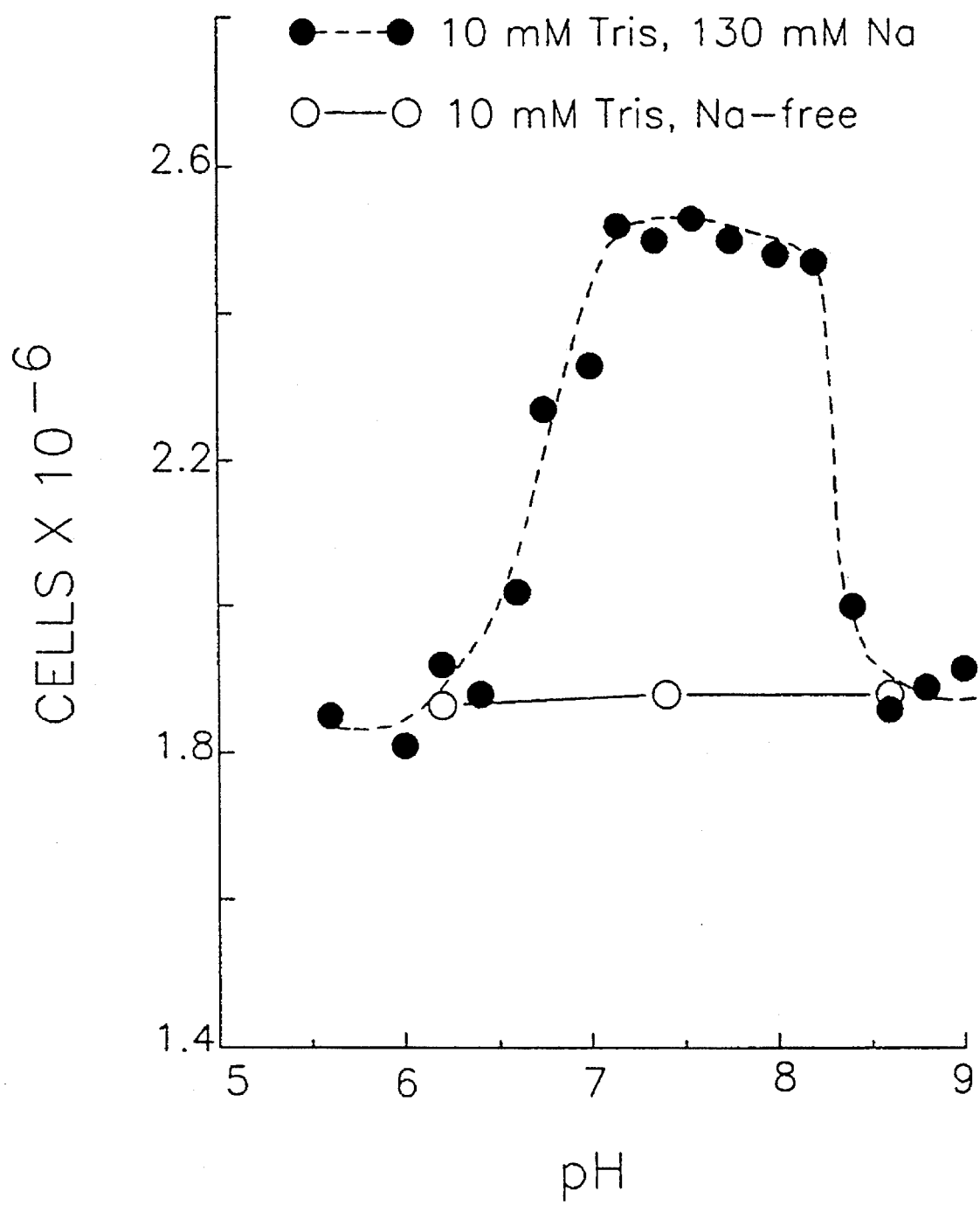
FIG. 15. Effect of pH and Na concentration on release of growth-promoting activity from the extracellular matrix (ECM) of BSC-1 cells.

The LSGF can also be released from ECM by low-$Na^+$ Tris-buffer (pH 6.6–8.2). FIG. 15 illustrates the effect of pH and Na concentration on release of growth-promoting activity from ECM of BSC-1 cells. Cultures were grown to confluence and the cell monolayer was removed with EGTA to expose ECM. Five ml of 10 mM Tris-buffer containing 130 mM NaCl was added to a dish coated with ECM and incubated for 10 minutes. The solution was then removed, an aliquot (250 µl) was added to a fresh culture, and the number of cells was counted 4 days later. Each value is the mean of 3 cultures; the variance is <5%. A reduced concentration of $Na^+$ (130 mM) and physiological pH appear to be the critical determinants for release of autocrine growth factor (LSGF) from the ECM. These results indicate that LSGF are stored in the ECM and can be released from this site by a reduction in the extracellular Na concentration.

The possibility that LSGF could be related to the fibroblast growth factor (FGF) family of proteins which are localized in the ECM was considered (Vlodovsky et al., 1987; Gospodarowicz et al., 1987). LSGF (approximately $M_r 6,000–7,000$) is much smaller than the 7 members of the FGF family which have apparent $M_r > 15,000$. FGFs were not detected in conditioned medium using immunoassay and also differ from LSGF with regard to charge; the former bind to cation exchange columns, whereas LSGF bound to an anionic exchanger (Walsh-Reitz et al., 1986; Gospodarowicz et al., 1985; Thomas, 1987). Finally 54-amino acid domains of the known acidic and basic FGF sequences (Jaye et al., 1986) were compared with the amino acid composition of LSGF (Table 1); no evidence of homology was apparent.

LSGF are smaller than a low K growth factor ($M_r 12,000–30,000$), reported previously, and are resistant to 56° C. for 30 minutes and freezing and thawing, both of which inactivate the low-K factor.

An apparently novel growth-promoting activity released from BSC-1 cells exposed to adenosine diphosphate also differs from LSGF because the former factor is much larger ($M_r 30,000–100,000$), is totally inactivated by DTT, and partially inhibited (50%) by heating to 56° C. for 30 minutes. Thus, LSGF appear to differ chemically and physiologically from known BSC-1 cell mitogens. The presence of LSGF did not permit BSC-1 cells to grow in soft agar indicating that the factor did not transform the cells. Addition of TGF-β2 (6 ng/ml) neutralized the growth-stimulating effect of LSGF.

Characterization of Autocrine Growth Factors

The biological activity of LSGF in conditioned medium was resistant to freezing for several weeks and to heating to 56° C. for 30 minutes but was destroyed by boiling for 15 minutes. Activity was stable in 1% acetic acid and in the pH range from 3.1 to 9.5. The activity was destroyed by exposure to trypsin (100 μg/ml) for 3 hours at 37° C., but was resistant to treatment with 65 mM dithiothreitol (DTT) for 1 hour at 22° C. The mitogenic activity of conditioned buffer or purified LSGF was destroyed by addition of TFA alone for about 1 hour, or in combination with acetonitrile or isopropanol.

Resistance to DTT differentiates the autocrine growth factors of the present invention from EGF, TGF-α, insulin, and insulin-like growth factors I and II that were inactivated by this reducing agent. In addition, $M_r$6,500-LSGF appeared distinct from known polypeptide mitogens for BSC-1 cells because 50 μl of crude LSGF in the presence of a maximal amount of either EGF (50 ng/ml), TGF-α (25 ng/ml), or insulin (5 μg/ml) exerted an additive effect on cell multiplication.

Other properties of the autocrine growth factors of the present invention are as follows:

(a) HPLC-purified LSGF labeled with IODO-GEN [$^{125}$I] have an apparent $M_r$~6,500.

(b) Purified LSGF exert their maximal mitogenic effect on BSC-1 cells at a relatively low extracellular concentration compared to known growth factors of similar size; as little as 1.25 ng/ml of LSGF exerted a maximal stimulatory effect on multiplication of confluent cells. This concentration of growth factor is considerably lower than for TGF-α ($M_r$=5,616) (25 ng/ml) or EGF ($M_r$=6,045) (50 ng/ml). The order of relative mitogenic potency on a molar basis is: LSGF ($0.21 \times 10^{-9}$M)>TGF-α ($4.5 \times 10^{-9}$)>EGF ($8.3 \times 10 \times 10^{-9}$).

(c) Three hours of exposure to LSGF is sufficient to elicit a maximum mitogenic response by BSC-1 cells.

(d) LSGF induce a rapid increase in the amount of an immunoassayable novel cytosolic protein that activates the glycolytic enzyme glyceraldehyde-3-phosphate dehydrogenase.

Amino Acid Composition of LSGF: Comparison with Other Peptide Growth Factors Amino acid compositional analysis on 4 different samples of LSGF was obtained by subjecting 15–260 pmoles of protein to hydrolysis with 5.7M HCl under oxidizing (n=1) or nonoxidizing (n=3) conditions. The hydrolysate was derivatized with phenylisothiocyanate, and HPLC separation was conducted on a C18 RP HPLC column. The information obtained is presented in Table 1 as the molar ratio of amino acids in the protein, and the values are compared with known peptides in Table 1 as the molar ratio of amino acids in the protein. The values are compared with known peptide growth factors of similar size. The LSGF of the present invention are clearly growth factors that have different properties than those of previously reported growth factors.

Several features of the amino acid composition of LSGF of the present invention are of interest. First, the data confirm the conclusion reached from biological assays: (1) that they differ from known growth factors of similar size; (2) the number of methionine residues in the 25-minute LSGF isoform (two) is greater than that observed in the other growth factors (Table 1), and indicates that the protein is a suitable candidate for cleavage with cyanogen bromide; third, the 3 arginine and 2 lysine residues suggest that cleavage of the protein with either clostripain, which cuts after arginine residues, endoproteinase Lys-C, or trypsin is a convenient approach to obtaining a fragment(s) for sequence analysis. Finally, the 23-min. and 25-min. Each LSGF isoform has a single cysteine moiety, whereas each of the other 5 growth factors have 6 of them. This would account for the biological resistance of LSGFs to DTT which inactivates the other growth factors, presumably by reducing disulfide bridges formed by the cysteine residues.

Sequencing the Autocrine Growth Factors

To obtain amino acid sequence information, about 5 nmoles of LSGF protein can be cleaved with cyanogen bromide at methionine residues. This is a simple and nearly quantitative method (Gross, 1967). Amino acid compositional analysis indicated that there are 2 methionine residues in the protein so that complete cleavage would be expected to yield 3 fragments. Although purification of fragments that result from cyanogen bromide cleavage can sometimes be difficult because fragments are not soluble, the peptides from this 6,500 Mr-protein are expected to be small enough that they are likely to be soluble. The cleavage fragments are separated by gel filtration on an HPLC size-exclusion column as a first step. This approach allows selection of peptides of a useful size and avoids pursuit of very short peptides. The lyophilized digest is dissolved in 20% acetic acid, centrifuged, and the supernatant applied directly to the column. Following chromatography, fractions of interest are dried and dissolved in 50 μl of acetic acid for application to the microsequencer. If the first round of chromatography is not sufficient to completely resolve a fragment of interest the procedure may be repeated several times without a major loss of material. If additional separation is necessary, RP HPLC with a linear gradient of acetonitrile in 0.1% TFA as an eluant as described herein may be used. This solvent provides good resolution when small fragments are prepared. A wavelength of 214 nm has been particularly sensitive and convenient to monitor the appearance of peptides. Fractions containing well-resolved peaks are lyophilized, dissolved in 20% acetic acid, and applied to a gas-phase microsequencer. A yield of 0.5–1.0 nmoles of a LSGF protein fragment is generally acceptable. This is more than sufficient to obtain amino acid sequence information, although as little as 50 pmoles of protein would be adequate.

Another approach to sequencing is to employ proteolytic cleavage with clostripain, endoproteinase Lys-C, or trypsin. The data presented in Table 1 indicates that LSGF has 3 arginine and 2 lysine residues which suggests that cleavage with a proteolytic enzyme which cuts after one of these amino acids is a useful approach. 5 nmole of LSGF are treated with clostripain (Mitchell, 1967). This protease has a restricted specificity so that it cuts only after arginine residues. Alternatively, proteolytic cleavage is carried out with endoproteinase Lys-C, which cleaves only after lysine residues (Jekel et al., 1983). The peptides produced by these enzymes are usually soluble, and are likely to be long enough to yield good oligonucleotide probe sequences. An additional advantage of clostripain is that the products produced by the enzyme are unlikely to contain internal arginine residues. Because arginine is encoded by 6 different triplets of bases, it is convenient to avoid it in the middle of the peptide fragment. Other enzymes such as modified trypsin (Promega) and V8 protease are also useful for effecting cleavage (Wilkinson, 1986).

Microsequencing of Autocrine Growth Factors

To obtain partial protein sequence, 400 pmoles of each HPLC-purified isoform of LSGF were applied to the gas-phase microsequencer for $NH_2$-terminal Edman degradation on at least 4 different occasions. The results indicated that the protein was blocked at the $NH_2$-terminus. Thus in order to obtain partial sequence information it is necessary to fragment the peptide as described in the following Sections.

1. Cleavage with Proteinase K

Fragmentation of the autocrine growth factors may be achieved by use of proteinase K. Proteinase K is a serine protease that exhibits a broad specificity because it hydrolyzes peptide bonds adjacent to the carboxylic group of aromatic and aliphatic amino acids. Evidence that Proteinase K cleaved [$^{125}$I]LSGF denatured with 1% SDS was obtained by running the reaction mixture on an SDS-polyacrylamide gel, and then preparing an autoradiogram. The autoradiographic signal emitted by untreated LSGF at $M_r$~6,500 was eliminated by protease treatment, and was replaced by a weak radioactive signal distributed between the tracking dye and $M_r$ <3,000. Thus LSGF of the present invention are susceptible to protease digestion.

2. Carbohydrate content

To test the hypothesis that LSGF are glycoproteins, the periodic-acid Schiff (PAS) stain was used as a probe for carbohydrates. This approach was chosen because the amount of material available is too small for gas chromatographic analysis, and the method was used successfully to detect carbohydrate on a novel $M_r$~8,700 glycoprotein inhibitor of angiogenesis (Taylor et al., 1985). PAS was used to stain apolipoprotein (apo) AII which contains 0–5 sialic acid residues per chain length of $M_r$~8,700. The color formation was apoAII concentration dependent; 5 µg of apo AII provided a much stronger signal than did 1 µg when stained on glass fiber filters, which indicated that the assay was quite sensitive. The presence of a positive PAS stain with 1 µg of apo AII and no stain with 1 µg of LSGF suggests that LSGF are not glycoproteins.

3. Phosphate content

To determine if LSGF are phosphorylated, 0.5 µg protein was treated with 2.5 units of calf intestine alkaline phosphatase at pH 8.0 for 6 hours at 37° C., and then loaded onto a reversed-phase HPLC column. No apparent difference in retention time between alkaline phosphatase-treated and untreated LSGF was detected for either the 23-minute or 25-minute isoforms. This result was interpreted to indicate that there is no phosphate accessible to the enzyme on the surface of the LSGF molecule.

Cloning the Genes Coding for Autocrine Growth Factors

Three different cloning strategies are within the scope of the present invention; (i) if the sequence of a 25 amino acid fragment of LSGF is obtained, the mixed oligonucleotides primed amplification of cDNA (MOPAC) procedure will be used to generate a probe, and then used to screen a BSC-1 cell cDNA library in lambda gt10 (preferred strategy) (Lee et al., 1988); (ii) if a peptide sequence of less than 25 amino acids is defined, degenerate oligonucleotides are synthesized and used to screen a BSC-1 cDNA library in lambda gt10; or (iii) a polyclonal monospecific rabbit antiserum (prepared as described below) raised against purified LSGF is preferably used to screen a BSC-1 cDNA library in lambda gt11.

In a collaborative study of another protein (Aithal et al., 1983) MOPAC was used to prepare a specific cDNA probe (Lee et al., 1988). In that instance microsequencing defined the amino acid sequence of a 25-mer peptide from which degenerate sense and antisense 20-mer oligonucleotides were synthesized for use as primers. BSC-1 cell poly(A)+ RNA was used to generate cDNA which served as a template for the polymerase chain reaction (PCR). The primers were annealed to the cDNA and PCR was carried out using Taq polymerase. The newly synthesized PCR product spanning the primers was unique and encoded a stretch of 5 amino acids that had been identified by microsequencing. This PCR product was used as a probe to screen a cDNA library for a full-length clone, a procedure that is advantageous as a cDNA cloning strategy.

In embodiments where microsequencing provides information about one or more LSGF, peptide fragments that are less than 25 amino acids in length, then the longest fragments are preferably used to design oligonucleotide probes. Choice of codon selection employs the most frequently used codon sets based upon tabulated codon used frequencies (Lathe, 1985). Probes complementary to the mRNA sequence of the protein are used to screen a BSC-1 cDNA library by hybridization techniques. Initially, cDNA libraries that have previously been prepared from BSC-1 cells grown under various physiological conditions are screened. cDNA libraries are prepared as described below.

Isolation of RNA

Total RNA may be isolated from BSC-1 cells by lysing them in guanidinium isothiocyanate and pelleting through a CsCl cushion (Chirgwin et al., 1979). The RNA is resuspended in sodium acetate and precipitated with ethanol. Oligo-dT chromatography is used to select the poly(A)+ fraction (Aviv and Leder, 1972) to construct a cDNA library in the phage insertion vector lambda gt10 (Watson and Jackson, 1984). Complex libraries containing at least $10^6$ recombinant plaques are generally obtained which are generally sufficient to detect even those mRNAs present at a very low level. The first strand cDNA is synthesized using random-hexamer priming. RNAse H and DNA polymerase I are used to replace the RNA strand of the mRNA-cDNA hybrid with DNA (Gubler and Hoffman, 1983). After methylation of EcoRI sites, flush ending with T4 polymerase, addition of linkers and their subsequent cleavage with EcoRI, the ds-cDNA is separated from the digested linkers by chromatography. The ds-cDNA is cloned into the EcoRI site of the vector using predigested lambda gt10 arms, packaged in vitro (Gigapack Gold), and plated onto E. coli C600 Hfl to select against wild type phage. Another aliquot of mRNA is used to construct a cDNA library in lambda gt11 for immunoscreening.

Screening the cDNA libraries

The cDNA library in lambda gt10 is screened with at least 2 different [$^{32}$P]oligonucleotide probes to identify clones of interest. From the initial cDNA clone(s), the cDNA library is further screened to obtain longer clones as well as those that extend more 5' and 3' to the original clone(s). The Sanger dideoxy sequencing method is used to determine the nucleotide sequence of the cDNA (Sanger et al., 1977). A start codon (ATG) and an open reading frame as well as a poly(A)+additional signal (AATAAA) from the cDNA sequence are information used to predict the protein sequence.

Alternatively, a monospecific antibody may be used to immunoscreen a cDNA library prepared in lambda gt11 (Young and Davis, 1983). Identification of a DNA sequence in a positive clone which encodes a stretch of amino acids defined by microsequencing of one or more peptide fragments provides evidence that cDNA of interest has been isolated. The size of LSGF (about 54 amino acid residues) does not necessarily predict that the mRNA encoding the protein is small. In the case of TGF-α for example, a polypeptide containing 50 amino acids is encoded by a relatively large mRNA of approximately 4.5 kilobases (Derynck et al., 1984). TGF-α is synthesized as part of a larger precursor peptide which contains 160 amino acids.

Confirmation that Probes Code Autocrine Growth Factors

To confirm that isolated cDNAs that screen positively with different sets of mixed probes do encode LSGF, certain mRNA is selected (Parnes et al., 1981) and translated in vitro (initially using a rabbit reticulocyte lysate). The objective is to immunoprecipitate a protein whose $M_r$ is about 6,500. The monospecific antiserum raised against purified LSGF is preferable for this purpose because it should react with several epitopes on the protein moiety. If LSGF have precursor forms, the in vitro translation product may be larger than the mature growth factor. This may be ascertained by using immunoblotting techniques as described below. In addition, the cDNA may be transcribed in vitro or in vivo (Xenopus oocytes) and the resulting mRNA translated as has been done by others (Nakai et al., 1988; Kayano et al., 1990).

Isolation of Genomic Clones Corresponding to LSGF Protein

The cDNA clones are used as probes in a Southern blot analysis to determine whether there is more than one copy of the autocrine growth factor (designated LSGF) genes. The cDNA clones are used to screen a BSC-1 DNA genomic library constructed in lambda EMBL3 using partial Sau3A digests. The genomic clones are characterized using restriction mapping, and hybridization of restriction digests of genomic clones to cDNA probes derived from different regions of the cDNA. This data provides information on the intron-exon genetic structure (Szostak et al., 1979). Detailed analysis of the intron-exon boundaries is obtained by specific oligonucleotide-primed sequence analysis of the genomic clone.

Structure of the LSGF mRNA cDNA clones, after they are identified and sequenced, are used to determine the size of the mRNA encoding the protein by Northern blot analysis, a technique well known to those of skill in the art (Kayano et al., 1990).

The amino acid sequence deduced from the nucleotide sequence of the cDNA clone is compared with the sequences of cleaved peptides determined by Edman degradation. A computer search using GENBANK, NBRF and other databases is conducted at the level of both nucleotides and amino acids to detect sequence similarities with known proteins. Similarities to functional domains of known proteins provide evidence of a general class to which the protein belongs, e.g., other growth factors, or oncogene products.

Preparation of Antibodies Directed Against Autocrine Growth Factors

Bioactive LSGF contained in the 24% isopropanol peak eluted from a RP HPLC column shown in FIG. 6 were subjected to vacuum centrifugation to remove isopropanol, and the resulting solution was neutralized to pH 7.0. This material (~8 μg LSGF) was emulsified in Freund's adjuvant and then aliquots were injected subcutaneously into each of two NZW white rabbits at 10 different sites. Two booster doses of LSGF were given intravenously; one after six weeks (7 μg) and another at 14 weeks (5 μg) following the primary dose. The antibody was prepared in the form of a 40% ammonium sulfate ($NH_2SO_4$) cut of whole rabbit serum. The serum was twice precipitated with $NH_2SO_4$ and the washed precipitate was resuspended in 50 mM Tris buffer (pH 7.4) to a final concentration of 40 mg/ml. The cut is referred to as "IgG" because it contains the IgG fraction of the serum, although it contains IgG molecules directed against antigens other than LSGF in addition to other proteins.

Figure 16:
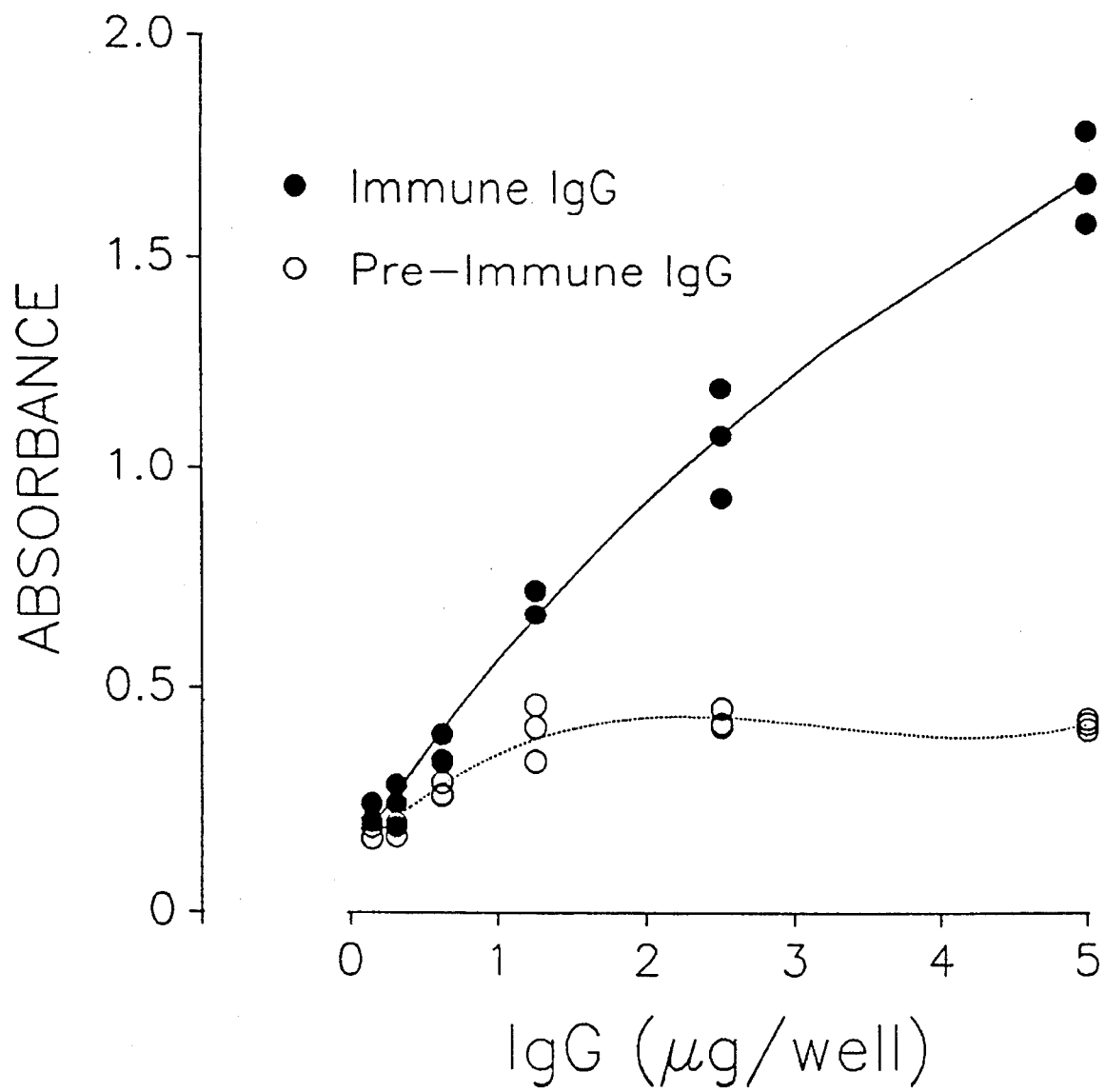
FIG. 16. Detection of LSGF with rabbit antiserum by an ELISA.

The interaction between LSGF protein and antibody was standardized using an ELISA protocol. FIG. 16 depicts the titration of 0 to 5 μg of immune and pre-immune IgG protein ($NH_2SO_4$ cut) per well. Each well was coated with 50 ng of the 25-minute isoform of LSGF protein. On the ordinate is plotted the absorbance at 450 nm after 30 minutes using an alkaline phosphatase detection system with p-nitrophenylphosphate as substrate with a Vectastain kit. The graph shows that the capacity of anti-LSGF IgG to detect LSGF is nearly linear in the range of 0.15 to 5 μg of IgG which is not the case for pre-immune IgG. A similar result was obtained with the 23-minute isoform. Neither immune nor pre-immune IgG was active against albumin or aprotinin ($M_r$6, 512).

Figure 17:
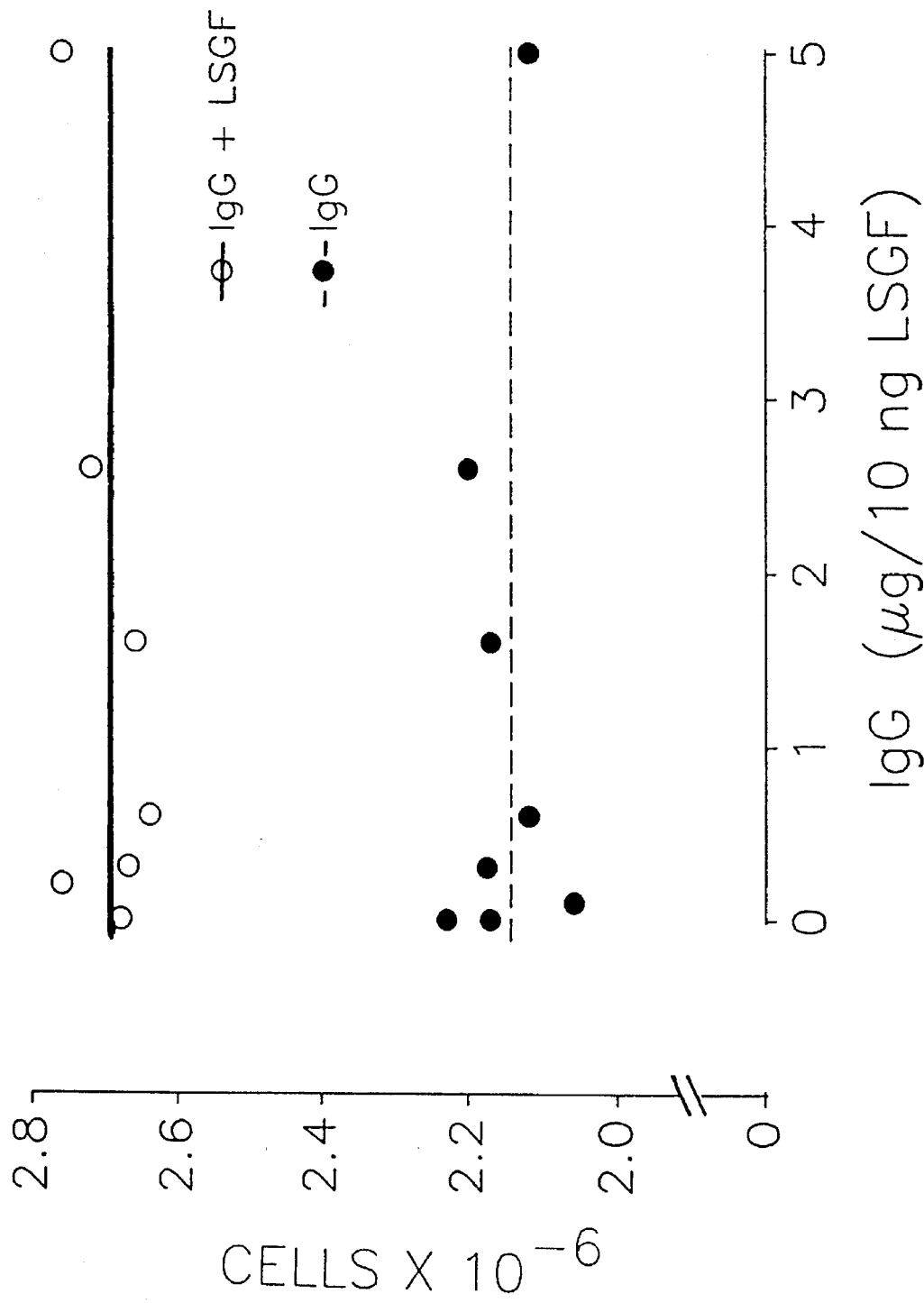
FIG. 17. Effect of anti-LSGF pre-immune serum on the growth-promoting activity of LSGF.

To validate the specificity of the anti-LSGF serum its capacity to neutralize the growth-promoting activity of both isoforms of HPLC-purified LSGF was assessed using BSC-1 cells. FIG. 17 shows that incubation of LSGF with pre-immune serum does not block the multiplication-stimulating effect of the 25-minute isoform of the growth factor; P<0.0001 (unpaired two-tailed t-test). In contrast, anti-LSGF IgG inhibits the growth-promoting effect of both the 25-minute isoform (FIG. 18) and the 23-minute isoform (FIG. 19).

As a positive control, murine EGF and a commercially prepared rabbit EGF antiserum were used in place of LSGF and anti-LSGF serum under identical experimental conditions. The anti-EGF serum totally blocked the growth-promoting activity of EGF but not LSGF.

IgG was also prepared by Protein A affinity chromatography from rabbit immune and pre-immune serum against LSGF. The ELISA was used to quantitate and compare the capacity of these IgGs to detect the growth factor. Immune IgG was nearly 17-fold more sensitive than pre-immune IgG in its capacity to detect LSGF.

A monospecific antibody to LSGF is useful in immunoassays to study the physiology of the protein. This antibody acts as an inhibitor of LSGF when bound to that protein.

To study the contribution of LSGF to growth control, the monospecific polyclonal antibody is used. The antibody is characterized by dot blotting, ELISA, immunoprecipitation, and Western blotting, procedures well known to those of skill in the art. Initially, an immunoassay is developed to define the time course and amplitude of the appearance and disappearance of LSGF in the extracellular fluid of BSC-1 cells exposed to the low Na signal.

Production of Monospecific and Monoclonal Antibodies

Because LSGF proteins are generally small, approximately $M_r$ 6,000–7,000 daltons, it is preferable to increase their immunogenicity by coupling the protein to keyhole limpet hemocyanin (KLH) prior to immunizing animals. Rabbits are given multiple intradermal injections of an initial total of 50 μg of LSGF protein coupled to KLH in Freund's complete adjuvant, followed at three-week intervals by booster immunizations in Freund's incomplete adjuvant (Hurn and Chantler, 1980). The protein may also be coupled to PPD, as described by Lachmann et al., (1986)

Screening of antibody titers is performed using an ELISA employing peroxidase-labeled anti-rabbit antiserum, and diaminobenzidine as substrate (Aithal et al., 1988). Colorimetric quantitation is done on a microELISA plate reader. Preimmune serum is collected and used as a control for comparison of titers. Positive antisera is tested for antibodies to LSGF protein in several ways. First, antisera is tested by immunoblotting analysis of low-Na conditioned buffer and fractions obtained during the purification procedure to determine specificity and sensitivity of the antisera. Crude and purified samples of LSGF are electrophoresed on 10% SDS-polyacrylamide gels and then transferred to an Immobilon PVDF membrane (Aithal et al., 1988). Adequacy of transfer is assessed by staining the gel with amido black. The PVDF paper is blocked with Tween-Tris-saline buffer and overlaid with a 1:100 dilution of antiserum. Binding of the antibody to the PVDF paper is assayed either with a peroxidase-labeled anti-rabbit antiserum, and chloronaphthol as the colored substrate, or with [$^{125}$I]labeled anti-rabbit antiserum followed by autoradiography. ECM and cytosolic extracts prepared from rat kidney tissue under each condition are tested for LSGF immunoreactivity. If reactivity is found, frozen sections of rat kidney will be prepared and stained by the sensitive alkaline phosphatase:anti-alkaline phosphate (APAAP) technique described by Cordell et al. (1984) to determine the distribution of LSGF protein with respect to different zones of the organ (e.g., cortex, medulla, papilla), site within the nephron (collecting duct, loop of Henle, proximal tubule), and cell type.

In other embodiments, the invention concerns the preparation of antibodies to the autocrine growth factors and species derived therefrom, either recombinant or non-recombinantly prepared. For example, it is contemplated that antibodies prepared against the autocrine growth factors disclosed herein, or other non-human species such as bovine or porcine, will have certain advantages over antibodies prepared against the human species, particularly in embodiments where an immuno-binding of reduced strength is desired.

Compositions which include monoclonal antibodies of the present invention may be prepared by first fusing spleen cells of a rodent with myeloma cells from the same rodent species, wherein the rodent providing the spleen cells has been immunized with the autocrine growth factor or antigenic segment thereof, its precursor, or related peptides. The rodent species utilized will generally be a mouse, particularly where one seeks to make an antibody against the autocrine growth factors. Of course, where an autocrine growth factor is prepared which incorporates structural variations, one will likely be able to successfully employ a hybridoma system according to the species of interest.

Antibodies may recognize higher molecular weight peptides that could be precursor forms of LSGF. To look for precursor forms, cells are exposed to [$^{35}$S] methionine, followed by a "chase" with cold medium, and LSGF is immunoprecipitated at successive times using the polyclonal antiserum that could recognize several determinants on the molecule. Immunoprecipitates are displayed on SDS-polyacrylamide gels, and the molecular weights of labeled peptides formed during the chase compared. Immunoprecipitation is carried out using either the method of Ohashi et al. (1982), in which the complexes are precipitated with glutaraldehyde-fixed S. aureus, or the method of Mellman and Galloway (1983), which uses anti-mouse antibody coupled to Sepharose. Labeling of a higher molecular weight peptide that is broken down with time to a peptide corresponding to the released form of LSGF provides evidence of a precursor form that is subsequently processed to yield LSGF.

In addition, the present invention provides a method for isolating autocrine growth factors from other species which may be found antigenically cross-reactive with those of canine and monkey cells. This method includes preparing an immunoadsorbent material having attached thereto an antibody to the growth factors. Numerous immunoadsorbent materials are known to those skilled in the art and include, for example, Affi-Gel, Cn-Sepharose, protein A-Sepharose, and numerous other well known immunoadsorbent techniques. All such techniques are applicable to the present invention and should prove useful in the isolation of the immuno cross-reactive species (for a more complete listing, see *Monoclonal Hybridoma Antibodies: Techniques and Applications,* John G. Hurrell, ed., CRC Press, 1982).

Immunoassays of LSGF

The antibody to LSGF is used to develop assays for quantifying the amount of LSGF in a single dish of cells. A dot immunobinding assay similar to that used by Jahn et al. (1984) is employed. In this assay, aliquots from cells solubilized in Triton X-100 or cytosolic fractions are blotted onto a nylon membrane in a dot-binding manifold. The membrane is fixed in acetic acid isopropyl alcohol, rinsed and blocked with BSA. Then the membrane is incubated in antibody solution, overlaid with [$^{125}$I]labeled Staph A or anti-mouse antiserum, and washed in Triton X-100. The individual samples are cut out and counted in a gamma counter. The assay is calibrated with measured amounts of purified LSGF protein. The calibration is repeated after the addition of cell lysates containing no activity to rule out any effects of cytosolic proteins on quantitation.

The immunoassay is used to measure the content of LSGF in extracts of ECM, cell lysates, and conditioned buffer of BSC-1 cells after exposure to low-Na medium. Primary cultures prepared from rabbit kidneys are employed to determine if normal diploid renal cells from other species are stimulated to release LSGF and proliferate in response to low-Na medium as do kidney cells of the established BSC-1 (monkey) and MDCK (canine) lines.

Immunological Detection of Autocrine Growth Factors

To detect LSGF with rabbit antiserum, an ELISA is used (a method well known to those of skill in the art). Currently, each well of a Linbro plate is coated overnight at 0° C. with 50 ng of LSGF in 100 μl of water. After washing the well with a buffer (PBS) 5 times, nonspecific binding sites are blocked using normal goat serum (400 μl) (Vector Lab) at 37° C. for 1 hour. After washing 5 times with PBS, anti-LSGF IgG is added (100 μl), and incubated at 37° C. for 2 hours. The color development is achieved using a Vectastain ABC-alkaline phosphatase kit and the absorbance at 450 nm is read. Examples of results are shown in FIG. 16.

Kits for the Detection of Autocrine Growth Factors

Moreover, kits may be provided in accordance with the present invention to allow for detection of the autocrine growth factors, in a biologic sample. Such kits would include polyclonal or monoclonal antibodies having specificity for the growth factors in combination with an immunodetection reagent. An immunodetection reagent is defined as any reagent for detecting or quantifying the formation of antibody/antigen complexes. Typical immunodetection reagents include the use of radiolabeled or enzyme-labeled antigens or antibodies. Techniques which incorporate labeled antibodies include, for example, RIA (radioimmunoassay) and ELISA (enzyme-linked immunosorbent assay). However, numerous other techniques are known which may be employed in immunodetection kits in accordance with the present invention. Patents which teach suitable techniques include, for example, U.S. Pat. Nos. 4,446,232; 4,407,943; 4,399,299; and 454,233.

Thus, a typical autocrine growth factor detection kit based on the ELISA technique could include the anti-growth factor monoclonal antibody or purified antigen (where one seeks to detect circulating antibodies), and a second "immunodetection" antibody capable of specifically immunoreacting with the purified antigen or anti-growth factor antibody. The second antibody could have a color-generating enzymatic activity associated with it, for example, an attached peroxidase molecule. When a second "immunodetection" antibody is employed in this fashion, one will generally first form an immunocomplex between the biologic sample to be tested, for example, serum, plasma, urine or tissue samples, and the antibody. After forming such an immunocomplex, the immunodetection antibody is added to react quantitatively with growth factors-bound antibody. This complex formation is then quantitated through the colorimetric peroxidase assay.

An alternative to using the above double-antibody technique, one may incorporate the enzyme or radio-ligand directly on the anti-growth factor antibody, and quantification made directly with the use of this directly labeled antibody.

The foregoing type of kit and method is well known and can be viewed generally as including the steps of obtaining a biologic sample contacting the biologic sample with anti-growth factor monoclonal antibody under conditions which will promote the formation of antibody/antigen complexes and detecting the formation of a specific immunologic reaction between the monoclonal antibody and the sample.

Neutralizing antibodies are also contemplated which, when bound to the autocrine growth factors or a segment thereof, render the enhancement capability of the growth factor non-functional.

Nucleic Acid Hybridization to Detect the Sequences Capable of Coding for the Autocrine Growth Factors, and Their Biologically Functional Equivalents The nucleic acid sequence information provided by the invention allows for the preparation of relatively short DNA (or RNA) sequences having the ability to specifically hybridize to gene sequences capable of coding for the autocrine growth factors of the present invention. In these aspects, nucleic acid probes of an appropriate length are prepared. The ability of such nucleic acid probes to specifically hybridize to the autocrine growth factors lend them particular utility in a variety of embodiments. Most importantly, the probes can be used in a variety of assays for detecting the presence of complementary sequences in a given sample. Other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 base nucleotide stretch of the sequences coding for autocrine growth factors. A size of at least 14 nucleotides in length helps to ensure that the fragment will be of sufficient length to form a duplex molecule that is both stable and selective. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production. Segments of from 18 to 25, or even 30 to 40 bases are also within the scope of this invention.

Accordingly, the nucleotide sequences of the invention are important for their ability to selectively form duplex molecules with complementary stretches of the gene. Depending on the application envisioned, varying conditions of hybridization may be employed to achieve varying degrees of selectivity of the probe toward the target sequence. For applications requiring a high degree of selectivity, relatively stringent conditions may be employed to form the hybrids, for example, selecting relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, preparation of mutants employing a mutant primer strand hybridized to an underlying template, or to isolate autocrine growth factor coding sequences from related species, functional equivalents, or the like, less stringent hybridization conditions are called for in order to allow formation of the heteroduplex. In these circumstances, conditions employed would be, e.g., such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, an enzyme tag such as urease, alkaline phosphatase or peroxidase, may be employed instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

One method of making molecules for detection of cell extracts is to use fluorescent probes. Fluorescent probes are well known to those skilled in the art. An example of a method is to bind fluorescein-labeled avidin (Vector Laboratories, Burlingame, Calif.) to a biotin-labeled protein. The signal may be enhanced.

Molecular Biology Methods of Preparing the Autocrine Growth Factors of the Present Invention Recombinant vectors are useful both as a means for preparing quantities of the autocrine growth factors encoding DNA itself, or as a means for preparing the encoded proteins. It is contemplated that where proteins of the invention are made from recombinant means, one may employ either prokaryotic or eukaryotic expression systems.

Where expression of autocrine growth factor coding nucleic acid segments in a eukaryotic host is contemplated, it may be desirable to employ a vector, such as a plasmid, that incorporates a eukaryotic origin of replication, as exemplified by vectors of the pCMV series, like pCMV4. Additionally, for the purposes of expression in eukaryotic systems, one will desire to position the autocrine growth factors encoding sequence adjacent to and under control of an effective eukaryotic promoter, such as an SV40 or CMV promoter. To bring a coding sequence under the control of a promoter, whether it be a eukaryotic or prokaryotic promoter, all that is generally needed is to position the 5' end of the transcription initiation site of the transcriptional reading frame of the protein between about 1 and about 50 nucleotides downstream of the promoter chosen.

Furthermore, where eukaryotic expression is contemplated, one will desire to incorporate into the transcriptional unit which includes the desired peptide or protein, an appropriate polyadenylation site (e.g., 5'-AATAAA-3'). Typically, the poly A site is placed about 30 to 2000 nucleotides "downstream" of the termination site of the protein at a position prior to transcription termination.

Useful eukaryotic vectors which include all of the foregoing, and into which the nucleic acid coding segments of the present invention can be inserted with little difficulty are well known. For example, suitable vectors include pCD and pCMV, with a preferred system being pCMV. In addition to pCD and pCMV vectors, other preferred eukaryotic expression vectors include pMSG and pSVL from Pharmacia LKB Technology, Piscataway, N.J. These utilize the MMTV and SV40 late promoters, respectively. cDNAs or nucleic acid segments can be readily inserted into one of the foregoing vectors via the HindIII restriction site (AAGCTT) "upstream" of (i.e., 5' of) the initiation codon (ATG) that begins translation of the encoded autocrine growth factors.

It is contemplated that virtually any of the commonly employed eukaryotic host cells can be used in connection with gene expression in accordance herewith. Examples include lines typically employed for eukaryotic expression such as AtT-20, HepG2, VERO, HeLa, CHO, WI 38, BHK, COS-7 RIN and MDCK cell lines.

Prokaryotic expression is an alternative which can be employed where desired. Although not required, where prokaryotic expression is envisioned, one will generally desire to employ a transcriptional unit which incorporates a reading frame corresponding only to the desired factor itself, represented by embodiments herein, so that further processing will not be required. Typically, prokaryotic promoters which may be employed include $P_L$, T7 and lac promoter, with T7 being generally preferred. Other preferred bacterial expression vectors include plasmid PKK233-2 and PKK233-3, available from Pharmacia LKB Technology. These utilize the tac and trc promoters, respectively.

Of course, even where a eukaryotic hook-up and expression is used, one will nevertheless desire to include a prokaryotic origin of expression, as well as selective markers operable in prokaryotic systems, to allow "shuttling" of sequences from construction in prokaryotic to expression in eukaryotes.

In certain embodiments, one may desire to simply prepare autocrine growth factors in accordance with the present invention by non-recombinant synthetic means, such as by chemical synthesis of peptides or a cell-free ribosomal "machine." Suitable peptide synthesizers are commercially available (Applied Biosystems), and may be employed. Alternatively BSC-1 cells may be grown on microcarriers (Biosilon®) to produce hundreds of liters of conditioned buffer from which LSGF would be isolated (Davies, P. F., 1981).

In certain embodiments of the invention it is contemplated that DNA fragments both shorter and longer which incorporate sequences other than those disclosed herein will find additional utilities, including uses in the preparation of short active peptides or even as short DNA fragment hybridization probes, e.g., in screening clone banks. In any event, fragments corresponding to the nucleic acid segments for stretches of as short as 14–20 or so nucleotides, will find utility in accordance with these or other embodiments. By having stretches of at least about 14 nucleotides in common with the nucleic acid segments coding for autocrine growth factors, or complements of the segments, a DNA segment will have the ability to form a preferential hybrid with autocrine growth factor DNA, particularly under more stringent conditions such as 0.15M NaCl and 0.02M sodium citrate pH 7.4 at 50° C. While a complementary or common stretch of about 14 or so nucleotides will ensure the ability to form a stable hybrid, longer stretches of complementarily may prove more desirable for certain uses. Thus, one may desire for certain uses DNA segments incorporating longer stretches of complementarily, for example, on the order of 18, 22 or even 25 or so bases.

Host Cell Cultures and Vectors

In general, prokaryotes are preferred for the initial cloning of DNA sequences and constructing the vectors useful in the invention. For example. E. coli K12 strain 294 (ATCC No. 314460) is particularly useful. Other microbial strains which may be used include E. coli strains such as E. coli B, and E. coli X 1776 (ATTC No. 31537). These examples are intended to be illustrative rather than limiting.

Prokaryotes may also be used for expression. The aforementioned strains, as well as *E. coli* W3110 (F-, lambda-, prototrophic, ATCC No. 273325), bacilli such as *Bacillus subtilus*, or other enterbacteriacea such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using PBR322, a plasmid derived from an *E. coli* species pBR322 contains genes for ampicillin and tetracycline resistance and thus provides easy means for identifying transformed cells. The PBR plasmid, or other microbial plasmid or phage must also contain, or be modified to contain, promoters which can be used by the microbial organism for expression of its own proteins.

The promoters most commonly used in recombinant DNA construction include the B- lactamase (penicillinase) and lactose promoter systems and a tryptophan (trp) promoter system. While these are the most commonly used, other microbial promoters have been discovered and utilized, and details concerning their nucleotide sequences have been published, enabling a skilled worker to ligate them functionally with plasmid vectors.

In addition to prokaryotes, eukaryotic microbes, such as yeast cultures may also be used. *Saccharomyces cerevisiase*, or common baker's yeast is the most commonly used among eukaryotic microorganisms, although a number of other strains are commonly available. For expression in Saccharomyces, the plasmid Yrp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the MRNA termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20 VERO and HeLa cells, Chinese hamster ovary (CHO) cell lines, and W138, BHK, COS-7 293 and MDCK cell lines. Expression vectors for such cells ordinarily include (if necessary) an origin of replication, a promoter located in front of (5' to) the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, HSV, BPV, CMV source, or may be provided by the host cell chromosomal replication mechanism. If the vector is integrated into the host cell chromosome, the latter is often sufficient.

Immunocytochemical localization of LSGF protein in normal, growing, and regenerating kidney tissue To determine if LSGF protein participates in renal growth during physiological and/or pathological states, immunoassays and immunocytochemical techniques are used to define the role of LSGF in kidney growth during (i) normal development in rats, (ii) regeneration after toxin-induced acute tubular necrosis (iii) compensatory hypertrophy and hyperplasia after uninephrectomy, and (iv) the onset, maintenance, and reversal of potassium depletion nephropathy. To determine if hyponatremia signals an increase in LSGF mRNA in vivo, kidney tissue from pregnant rats fed a low-Na diet are used because the serum Na concentration of these animals is reduced by 8–10 mM after 14 days of gestation. Experiments using the monospecific antibody to detect LSGF protein in specific types of cells in renal tissue complement studies using in situ hybridization. Studies using the antibody provide information about the steady-state accumulation of the protein in cells along the nephron, whereas experiments with the cDNA probe are used to identify cells in which the protein is induced. This dual approach is particularly helpful if the protein is constitutively expressed at a low level in vivo.

Inhibiting Effect of Anti-Autocrine Growth Factors

The effect of anti-autocrine growth factor (designated LSGF) pre-immune serum on growth-promoting activity of LSGF is shown in FIG. 17. The 25-minute isoform of LSGF that had been renatured in water was mixed with specified amounts of pre-immune IgG for 90 min at 37° C. A total of 25 ng LSGF was added to each confluent culture of BSC-1 cells. The number of cells was counted in a hemocytometer 4 days later. Pre-immune serum had no effect on the growth-promoting effect of LSGF. Each value is the mean cell count of 3 cultures. The variance was <5%.

Figure 18:
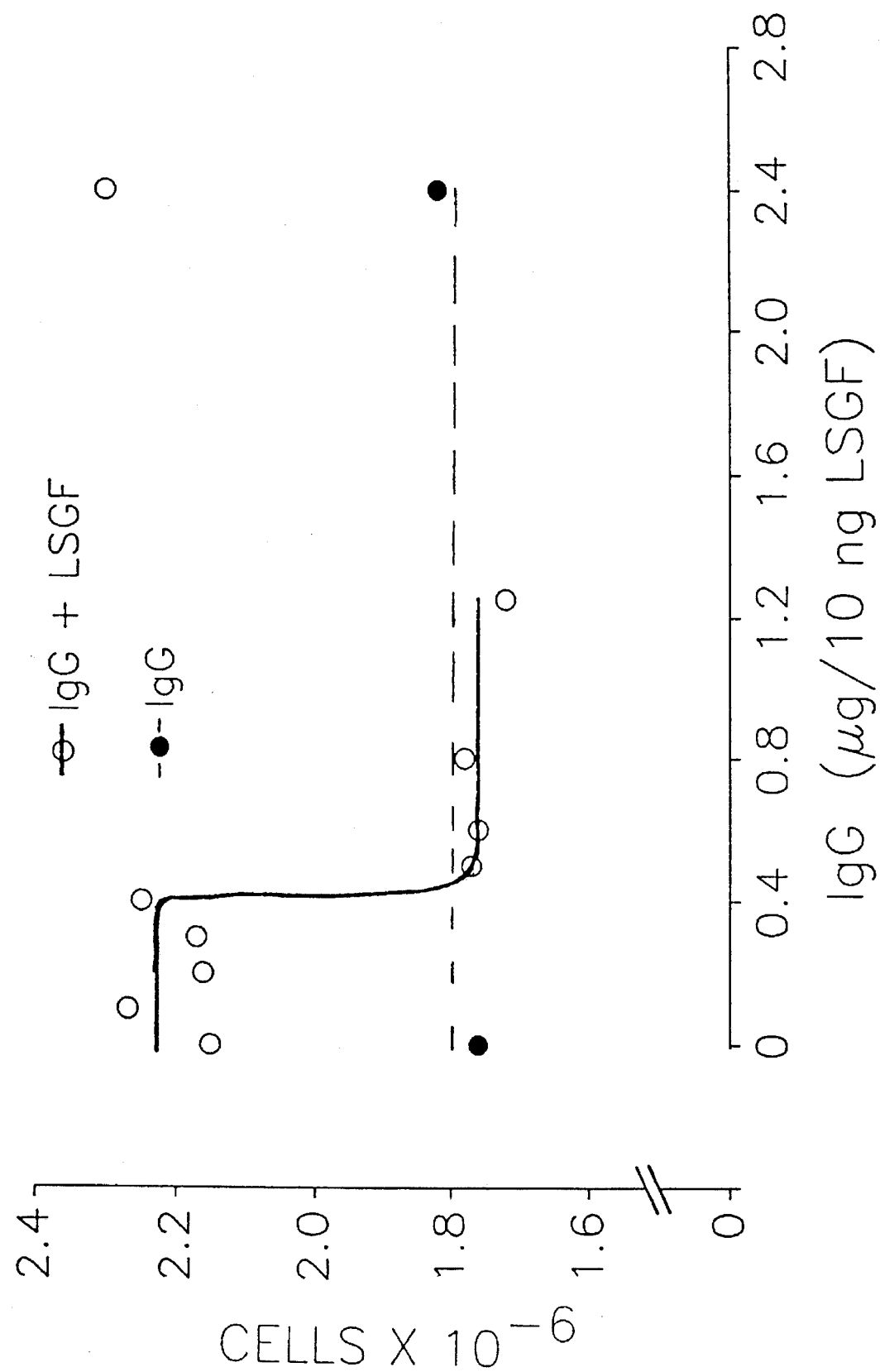
FIG. 18. Effect of anti-LSGF immune serum on the growth-promoting activity of a "25-minute" LSGF isoform.
Figure 19:
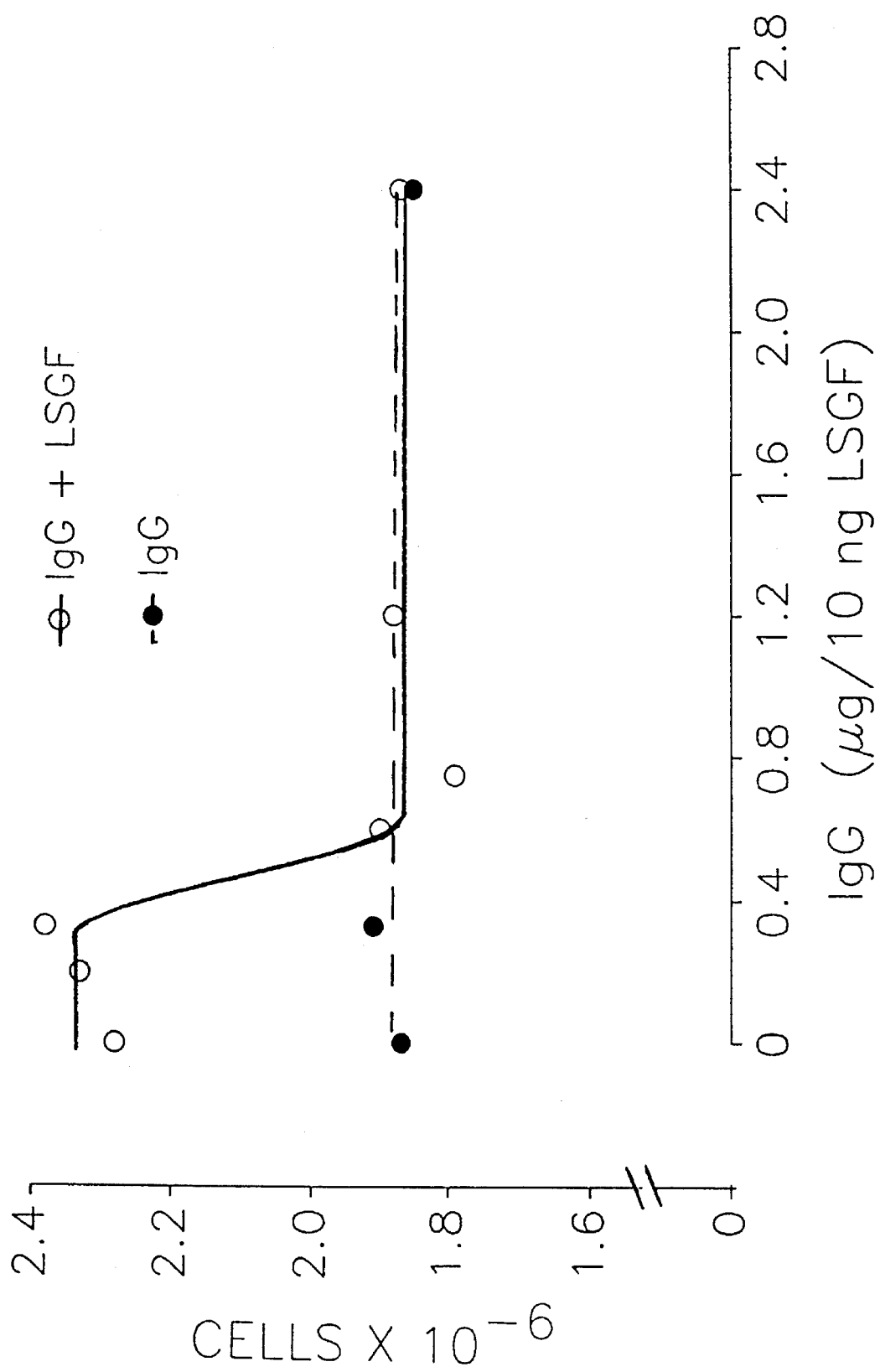
FIG. 19. Effect of anti-LSGF immune serum on the growth-promoting activity of a "23-minute" LSGF isoform.

The effect of anti-LSGF serum on growth-promoting activity of the 25-minute LSGF isoform is shown in FIG. 18. The experimental protocol used was as described for FIG. 17. Anti-LSGF serum at 0.5 µg IgG/10 ng LSGF completely neutralized growth-promoting activity. Each value is the mean cell count of 3 cultures. The variance was <5%.

The effect of anti-LSGF serum on growth-promoting activity of 23-minute LSGF isoform is shown in FIG. 19. The protocol used is as described for FIG. 18. Anti-LSGF serum at 0.6 µg IgG/10 ng LSGF completely neutralized growth-promoting activity. Each value is the mean cell count of 3 cultures. The variance was <5%.

In general, antibodies to LSGF are tested for their ability to inhibit the growth response of cells to low-Na medium, and the capacity of exogenous LSGF to reverse this growth inhibition. As controls, growth-inhibitory antibodies are tested for their ability to block the growth response of BSC-1 cells to other mitogenic stimuli as well. The antibodies are used on other types of cells (e.g., fibroblasts) to evaluate their capacity to inhibit the effect of known mitogens (e.g., insulin).

Detection of a Candidate Inhibitor Substance

In still further embodiments, the present invention concerns a method for identifying new autocrine growth factor inhibitory compounds, which may be termed as "candidate substances." It is contemplated that this screening technique will prove useful in the general identification of any compounds that will serve the purpose of inhibiting autocrine growth factors. It is further contemplated that useful compounds in this regard will in no way be limited to proteinaceous or peptidyl compounds. In fact, it may prove to be the case that the most useful pharmacologic compounds for identification through application of the screening assay will be non-peptidyl in nature and, e.g., which will be recognized and bound by the factors, and serve to inactivate the factors through a tight binding or other chemical interaction.

Thus, in these embodiments, the present invention is directed to a method for determining the ability of a candidate substance to inhibit autocrine growth factors, the method including generally the steps of:

(a) obtaining a composition comprising mitogenic growth factors;

(b) admixing a candidate substance with the mitogenic growth factors composition; and (c) determining the ability of the mitogenic growth factors composition to enhance cell growth.

Inhibitors are detected by their ability to reduce the cell growth enhancement effect of the autocrine growth factors. An important aspect of the candidate substance screening assay hereof is the ability to prepare growth factors composition in a relative purified form, for example, in a manner as discussed above. This is an important aspect of the candidate substance screening assay in that without at least a relatively purified preparation, one will not be able to assay specifically for growth factors inhibition, as opposed to the effects of the inhibition upon other substances in the extract which then might affect the growth factors. In any event, the successful isolation of the growth factors now allows for the first time the ability to identify new compounds which can be used for inhibiting this protein.

The candidate screening assay is quite simple to set up and perform, and is related in many ways to the assay discussed above for determining growth factors activity. This, after obtaining a relatively purified preparation of the growth factors, one will desire to simply admix a candidate substance with the growth factors preparation, preferably under conditions which would allow the growth factors to perform its cell growth enhancement function, but for inclusion of an inhibitory substance. Thus, for example, one will typically desire to apply the composition to cultured cells and compare their growth to that of cultures to which only the growth factor is applied.

Accordingly, one will desire to measure or otherwise determine the activity of the relatively purified growth factors in the absence of the assayed candidate substance relative to the activity in the presence of the candidate substance in order to assess the relative inhibitory capability of the candidate substance.

In still further embodiments, the present invention is concerned with a method of inhibiting growth factors which includes subjecting the growth factors to an effective concentration of an inhibitor such as one of a family of peptidyl compounds or with a candidate substance identified in accordance with the candidate screening assay embodiments. This is, of course, an important aspect of the invention in that it is believed that by inhibiting the growth factors, a mechanism for controlling cell growth will result.

Expression of the LSGF Gene in Renal Cells in Culture

Northern blot analysis is used to determine the level of mRNA for the LSGF gene as a function of time after BSC-1 cells are exposed to low-Na medium repeatedly at 5 minute intervals. If increased mRNA for LSGF is detected, nuclear run on studies are used to determine whether this is due to increased transcription or to stabilization/decreased degradation (Manly, 1984). The levels of mRNA are correlated with the amount of LSGF protein in the cell, culture medium, and ECM as determined by immunoassay. Thus, direct information is obtained on the amount of LSGF in BSC-1 cells and in ECM, and thereby elucidates which step (transcriptional, post-transitional, etc.) controls the critical event leading to its formation.

Cellular Localization of Autocrine Growth Factors

LSGF may be released and deposited in the ECM by exocytosis, or by other mechanisms. To determine whether the protein is present in secretory vesicles, two approaches are used. First, microsomal and cytosolic fractions of BSC-1 cells are obtained and the content of LSGF in each are measured by an immunoassay. If the microsomal fraction contains activity, the membranes are lysed by gentle sonication or osmotic disruption to determine whether activity is tightly or loosely associated with the membranes. Second, BSC-1 cells are permeabilized by methanol treatment, and incubated with anti-LSGF antiserum followed by peroxidase or gold-labeled second antibody (Roth, 1983). After development of the peroxidase (if used), cells are examined by electron microscopy to determine if the label is associated with intracellular vesicles. In this way the antibodies are expected to reveal whether LSGF immunoreactivity is present in secretory vesicles.

Effect of Autocrine Growth Factors on Na$^+$ and K$^+$ Content Cells

To determine if LSGF alters the net transport of Na$^+$ or K$^+$, its effect on Na$^+$ and K$^+$ content of BSC-1 cells may be studied. Measurements of Na$^+$ and K$^+$ content during the onset of mitogenesis (Walsh-Reitz et al., 1984) are carried out at 10 minute intervals for 2 hours. Experiments are performed in the absence of drugs such as amiloride or ouabain, which are known to alter cell cation fluxes. These measurements of cell Na$^+$ and K$^+$ content are performed by atomic absorption spectrophotometry as described previously (Walsh-Reitz et al., 1984). The intracellular fluid volume is estimated as the difference between the total volume of the cell monolayer as determined with [methyl-$^{14}$C] glucose and the extracellular fluid space measured with [$^3$H]inulin (Rindler et al., 1979). If an alteration in cell Na$^+$ content is detected, detailed studies are performed to identify specific determinants of Na$^+$ transport that could mediate this effect (e.g., Na$^+$ influx via Na$^+$/H$^+$ exchange) (Schuldiner et al., 1982). To determine, for example, if LSGF are ligands for the Na$^+$/H$^+$ antiporter in BSC-1 and other renal epithelial cells, isolated membrane vesicles from rat kidney cortex are used to determine if LSGF exerts an effect on Na$^+$/H$^+$ exchange. There may be an association between the mitogenic effect of LSGF and specific alterations in cation content that would focus attention on a few of the many factors that regulate monovalent cation transport. Importantly, LSGF is likely to stimulate mitogenesis by a mechanism that is independent of Na$^+$ or K$^+$ influx.

Receptor for LSGF

Knowledge about the receptor for LSGF is likely to be informative for determining the mechanism by which the factor stimulates growth thereby allowing manipulation of cell growth. The LSGF receptor is affinity labeled by cross-linking it to radioactive LSGF, using methods as described by Segarini et al. (1987). [$^{125}$I]LSGF are incubated with the cells for 3 hours at 4° C., the unbound factor is removed and the bound ligand is cross-linked to the receptor by adding 0.3 mM disuccinimidyl suberate. After washing the cells several times, the solubilized proteins are separated by SDS-PAGE. Autoradiography enables visualization of the size(s) of the receptor(s). For quantitation, binding is measured at increasing concentrations of LSGF, and any non-specific components are identified by measuring binding in the presence of a large excess of unlabeled growth factor. The specific binding is used to construct a Scatchard plot (developed by G. Scatchard in 1949, to show antigen binding to antibodies; a straight line results if all antibody-combining sites are identical and independent), to determine the affinity and numbers of receptors for LSGF.

Alternatively, an immunologic approach to identifying the LSGF receptor is a method used to isolate a chicken hepatocyte aggregation factor (Pannel et al., 1980). Monoclonal antibodies are prepared by injecting intact BSC-1 cells into Balb/c mice. This results in the generation of antibodies against cell surface proteins, including the LSGF receptor. Each clonal antibody obtained is tested for its capacity to inhibit LSGF activity. The inhibitory antibody binds to the receptor, thereby blocking the binding of LSGF and preventing initiation of DNA synthesis. This antibody is subsequently used to isolate and characterize the LSGF receptor. Immunoprecipitation of [$^{35}$S]methionine-labeled, or [$^{125}$I]labeled receptor protein, and subsequent analysis on SDS-PAGE could reveal the apparent M$_r$ of the receptor. An antibody affinity column is then prepared and used to isolate the receptor protein quantitatively for further characterization such as amino acid sequence analysis, and comparison to other known growth factor receptors.

Assessment of the Effect of Treating Kidneys with Autocrine Growth Factors

An animal model is available to assess the effects of treating damaged kidneys with compositions that include autocrine growth factors. (Toback, 1977; Toback et al. 1977).

An intravenous injection of 1.0 to 1.1 mg of mercury per kg of body weight as HgCl$_2$ is given to rats to induce a reversible syndrome of acute nonoliguric acute renal failure. After one day, there are marked increases in serum urea nitrogen concentration (SUN), urinary excretion of sodium and protein, and necrosis of proximal tubular cells. By day two, increases in phospholipid, DNA and RNA synthesis, and mitotic index indicate that cellular regeneration is underway. By day three, the SUN reaches a maximum, and squamoid epithelial cells appear on the tubular basement membrane. At day five, the SUN returns to normal, the maximal rate of phospholipid synthesis is reached, and the tubules are repopulated with more mature cells.

The effects of infusion of a composition of autocrine growth factors on renal structure is compared with untreated rats and animals infused with vehicle alone during the course of the mercuric chloride-induced acute tubular necrosis syndrome discussed above.

EXAMPLES

Example 1

ISOLATION AND PURIFICATION OF AUTOCRINE GROWTH FACTORS

In an illustrative embodiment of a method for isolating and purifying LSGF, 6 liters of low Na CM (conditioned medium) was prepared from 5 cell culture dishes containing confluent BSC-1 cells. Confluent cultures are those well known to those of skill in the art as cultures in which cell growth has reached a level whereby cells cover approximately the entire surface of the dish upon microscopic examination. Nunclon dishes that have a surface area of 500 cm$^2$ and volume of 125 ml each are a preferred embodiment to grow the cells. It is preferred that fluid is poured directly from the large dishes into silanized vessels for storage rather than transferred by aspiration.

Cultures of BSC-1 cells are plated and grown to confluence entirely in phenol-red free DMEM containing a relatively high Na$^+$ concentration (155 mM) compared to the Na$^+$ concentration which effects release of the autocrine growth factor from cells (130 mM Na$^+$), and 1.6 μM biotin, and 1% calf serum. For conditioning, the medium was replaced by low-Na$^+$ Tris-buffer (Na$^+$=130 mM, K$^+$ =5.4 mM, pH 7.4 for 4–5 minutes). The conditioned buffer (CB) (125 ml/plate) is collected and filtered through a 0.22 μm filter, and stored at 4° C. for further processing. The cells can be used repeatedly to generate biologically active material as long as the cultures are returned to their routine growing environment for awhile, e.g. if phenol-red free DMEM containing 0.5% serum is added back to the culture, and the plate is returned to the incubator for 24 hours. In an illustrative embodiment conditioned buffer (CB) containing the growth factor was harvested once a day for 5 days for each culture. The amount of growth-promoting activity released by the cells is unchanged during this period of time, as estimated by serial dilution of CB and assay of the aliquots on fresh cultures.

The ultrafiltration procedure has been scaled up so that an Amicon Diaflo spiral-wound membrane cartridge system is now used. Pooled CB may be ultrafiltered using sterile, distilled, deionized water through a YM 10 membrane to eliminate molecules with an apparent $M_r>10,000$ daltons, and then ultrafiltered with diafiltration using water and a YM 3 spiral filter that has a molecular weight cut off (MWCO) of 3,000 daltons. By this method approximately 6 liters of CB are processed to approximately 200 ml of ultrafiltrate ($3,000<M_r<10,000$) daltons within about 2 days. This material is then concentrated using an Amicon pressure cell fitted with a YM 2 membrane (MWCO of 1,000) that yields about 25 ml of concentrate which is divided into several aliquots, frozen at $-70°$ C., and lyophilized. About 0.25 mg protein per liter of CB results from this part of the protocol.

The bioactive material containing molecules with an apparent $M_r$ 3,000–10,000 daltons was subjected to HPLC on a Brownlee Spheri-5 RP-18 column as the first step in the chromatographic purification protocol. The column was eluted with a linear gradient of isopropanol (0–50%) in 0.01M phosphoric acid as the mobile phase. Fractions (1 ml) were collected and an aliquot of each one (5 µl) was assayed for growth-promoting activity on BSC-1 cells by performing cell counts and measurements of [$^3$H]thymidine incorporation into DNA, as described by Aithal et al. (1988). Growth-promoting activity was detected in the fraction which corresponded to a notched peak that appeared at ~24% isopropanol. To confirm purity, and to remove the isopropanol and phosphoric acid, the active material was applied to a Beckman Ultrasphere ODS column, and eluted with a linear gradient of acetonitrile (0–80%) in 0.1% TFA (FIGS. 8–10).

Example 2

EXTRACELLULAR LOCALIZATION OF LSGF

The LSGF were released into the medium after as little as 3 minutes of exposure to low-$Na^+$ medium. In addition, pretreatment of the cells with cycloheximide failed to prevent the appearance of growth-promoting activity which implied that new protein synthesis was not required for its release. These observations suggested that the factor was preformed, but provided no insight into whether it was released from inside or outside the cell.

To define the location of preformed LSGF 1 mM EGTA was added to detach cells from the dish (Harper and Juliano, 1980). The cell suspension was poured into a sterile tube containing 2 ml DMEM, 0.01% serum, and 1.6 µM biotin and was centrifuged gently. The cell pellet was resuspended in 5 ml low Na DMEM (130 mM) for 4.5 minutes, and CM was then collected by centrifugation, and filtered. An aliquot (250 µl) of CM was added to a fresh culture to assay for growth-promoting activity. No activity was detected, which suggested that the storage site of LSGF was elsewhere. To determine whether LSGF was stored in the extracellular matrix (ECM), ECM was prepared by growing confluent BSC-1 cells in 60-mm dishes under conditions used to prepare LSGF. To remove the cell monolayer, medium was aspirated and 2 ml of 1 mM EGTA in phosphate-buffered saline (pH 7.5) at 37° C. was added with periodic swirling. The cell-EGTA mixture was aspirated and the plate was rinsed 3 times with 5 ml of DMEM. Light microscopy revealed that no cells remained on the dish, and that its entire surface was coated with ECM. A test solution such as low-$Na^+$ DMEM (5 ml) or low Na Tris-buffer was layered onto the ECM for 4.5 minutes, poured from the dish into a polypropylene container, passed through a 0.22 µm Millex-GV filter into a sterile polypropylene tube, and stored at 4° C. until used. Aliquots were then tested for growth-promoting activity on recipient cultures of cells.

Example 3

IDENTIFICATION OF RENAL CELLS EXPRESSING THE GENE FOR LSGF PROTEIN IN SITU

To determine exactly which renal cells express the gene that encodes LSGF, in situ hybridization of labeled LSGF cDNA is used to probe tissue sections of rat kidneys. The method can also be extended to examine the effect of systemic $Na^+$ deficiency on expression of the LSGF gene in other tissues, such as rat liver and muscle, and in human renal tissue.

The technique of in situ hybridization has been used previously to study preproEGF gene expression in mouse kidney tissue (Atkin et al., 1990). Cells in the rat kidney expressing the gene for LSGF during the onset of growth following toxin-induced acute tubular necrosis are sought by in situ hybridization. Unique sequences of cDNA (or anti-sense mRNA) corresponding to the coding region are preferably used as probes. Rather than cross a species boundary by using monkey cDNA to probe rat renal tissue, the rat cDNA encoding LSGF are isolated for use in this study by cross hybridization. To further distinguish a specific signal from non-specific hybridization, one serial tissue section is treated with RNase prior to hybridization to remove all mRNA. Another section is treated with size-selected [$^{32}$P] labeled DNA from bacteriophage φX174 used as a "blank" and which yields only a few evenly dispersed silver grains over the tissue. An additional section is "hybridized" in the absence of probe to ensure that chemography is not produced (Moench et al., 1985). Another method of confirming that a hybridization signal is specific is to dilute the labeled probe with increasing amounts of unlabeled probe which also offers a semi-quantitative measurement of the mRNA. However, Northern blots are generally preferred for the quantitation of a mRNA species.

The preferred method (Atkin et al., 1990) is outlined briefly below. Rats are killed, the kidneys rapidly sectioned longitudinally to prevent artifacts from differential freezing, and then frozen in hexane/dry ice. The tissue is sectioned at −20° C. on a cryostat, and the 6 µm sections are removed with a subbed slide, and fixed in glutaraldehyde (4%) in 0.1M phosphate (pH 7.3) with ethylene glycol (20%). Single stranded anti-sense RNAs are generated in an in vitro transcription system. The cDNA is subcloned into Ribo-probe Gemini vectors (Promega Biotec), and both sense and anti-sense RNA labeled with [$^{35}$S]UTP are prepared. The prehybridization and washing procedures used are generally those described by Ingham et al. (1985). Due to the elimination of non-complementary labeled probe, and the higher thermal stability of RNA-RNA hybrids as compared to RNA-DNA hybrids, this method generally gives a higher signal to background ratio. Also, the sense strand serves as an ideal negative control. The slide is then dipped in Kodak NTB 3 film emulsion, stained with hematoxylin and eosin, and examined under a microscope.

The results of this method permit determination of the types of cells in renal tissue that express LSGF mRNA under control conditions, and whether the number and type of cells expressing the message changes during the onset of progression of renal regeneration after acute tubular necrosis in vivo. Assessment of the relative amount of hybridization per cell may also be carried out to compare gene expression in specific cell types under regenerating and control conditions.

REFERENCES

The references listed below are incorporated herein by reference to the extent that they supplement, explain, provide a background for, or teach methodology, techniques, and/or compositions employed herein.

Reference 1. Aithal, H. N., Walsh-Reitz, M. M., Kartha, S., Gluck, S. L., Franklin, W., Knigge, K. M. and Toback, F. G. (1988) *Amer. J. Physiol.* 255 24: F868–F873.

Reference 2. Aithal, H. N., Walsh-Reitz, M. M., Toback, F. G. (1983) *Proc. Natl. Acad. Sci. U.S.A.* 80:2941–2945.

Reference 3. Aithal, H. N., Knigge, K. M., Kartha, S., Czyzewski, E. A. and Toback, F. G. (1988) *Journal of Immunological Methods* 112:63–70.

Reference 4. Atkin, B. M., Franklin, W. A., Bell, G. I. and Toback, F. G. (1990) *Nephron* 54:313–317.

Reference 5. Aviv, H., Leder, P. (1972) *Proc. Natl. Acad. Sci. U.S.A.* 69:1408–1412.

Reference 6. Barsh, G. S., Cunningham, D. D. (1977) *J. Supramol. Struct.* 7:61–77.

Reference 7. Bindal, R. D., Katzenellenbogen, J. A. (1988) *J. Med. Chem.* 31:1978–1983.

Reference 8. Bindal, R. D., Carlson, K. E., Katzenellenbogen, B. S., Katzenellenbogen, J. A. (1988) *J. Steroid Biochem.* 31:287–293.

Reference 9. Brown, J. L., Roberts, W. K. (1976) *J. Biol. Chem.* 251:1009–1014.

Reference 10. Chirgwin, J. M., Przybyla, A. E., MacDonald, R. J., Rutter, W. J. (1979) *Biochemistry* 18:5294–5299.

Reference 11. Cordell, J. L., Falini, B., Erber, W. N., Ghosh, A. K., Abdulaziz, Z., MacDonald, S., Pulford, KAF, Stein, H., Mason, D. Y. (1984) *J. Histochem. Cytochem.* 32:219–229.

Reference 12. Davies, P. F. (1981) *Exp. Cell Res.* 134: 367–376.

Reference 13. Derynck, R., Roberts, A. B., Winkler, M. E., Chen, E. Y., Goeddel, D. V. (1984) *Cell* 38:287–297.

Reference 14. Gattone, V. H., Andrews, G. K., Niu, F. W., Chadwick, L. J., Klein, R. M., Calvet, J. P. (1990) *Dev. Biol.* 138:225–230.

Reference 15. Gospodarowicz, D., Lepine, J., Massoglia, S., Wood, I. (1984) *J. Cell Biol.* 99:947–961.

Reference 16. Gospodarowicz, D., Ferrara, N., Schweigerer, L., Neufeld, G. (1987) *Endocrine Rev.* 8:95–114.

Reference 17. Gospodarowicz, D., Massoglia, S., Cheng, J., Lui, G., Böhlen, P. (1985) *J. Cell Physiol.* 122:323–332.

Reference 18. Goss, R. J., Rankin, M. (1960) *J. Exp. Zool.* 145:209–216.

Reference 19. Gross, E. (1967) *Meth. Enzymol.* 11:238–255.

Reference 20. Gubler, U., Hoffman, B. J. (1983) *Gene* 25:263–269.

Reference 21. Hanks, S. K., Amour, R., Baldwin, J. H., Maldonado, F., Spiess, J., Holley, R. W. (1988) *Proc. Natl. Acad. Sci. U.S.A.* 85:79–82.

Reference 22. Harper, P. A., Juliano, R. L. (1980) *J. Cell Biol.* 87:755–763.

Reference 23. Holley, R. W., Amour, R., Baldwin, J. H. (1978) *Proc. Natl. Acad. Sci. U.S.A.* 75:1864–1866.

Reference 24. Holley, R. W., Amour, R., Brown, J. H. (1978) *Proc. Natl. Acad. Sci. U.S.A.* 75:339–341.

Reference 25. Holley, R. W., Böhlen, P., Fava, R., Baldwin, J. H., Kleeman, G., Amour, R. (1980) *Proc. Natl. Acad. Sci. U.S.A.* 77:5989–5992.

Reference 26. Holley, R. W., Amour, R., Baldwin, J. H., Brown, K. D., Yeh, Y-C (1977) *Proc. Natl. Acad. Sci. U.S.A.* 74:5046–5050.

Reference 27. Hopps, H. E., Bernheim, B. C., Nisalak, A., Tjic, J. H., Smadel, J. E. (1963) *J. Immunol.* 91:416–424.

Reference 28. Hurn, BAL, Chantler, S. M. (1980) *Meth. Enzymol.* 70:104–142.

Reference 29. Ingham, P. W., Howard, K. R., Ish-Horowicz, D. (1985) *Nature* (London) 318:439–445.

Reference 30. Izant, J. G., Weintraub, H. (1984) *Cell* 36:1007–1015.

Reference 31. Jahn, R., Schiebler, W., Greengard, P. (1984) *Proc. Natl. Acad. Sci. U.S.A.* 81:1684–1687.

Reference 32. Jaye, M., Howk, R., Burgess, W., Ricca, G. A., Chiu, I-M., Ravera, M. W., O'Brien, S. J., Modi, W. S., Maciag, T., Drohan, W. N. (1986) *Science* 233:541–545.

Reference 33. Jekel, P. A., Weijer, W. J., Beintema, J. J. (1983) *Anal. Biochem.* 134:347–354.

Reference 34. Kartha, S., Sukhatme, V. P., Toback, F. G. (1987) *Am. J. Physiol.* 252:F1175–F1179.

Reference 35. Kartha, S., Bradham, D. M., Grotendorst, G. R. and Toback, F. G. (1988) *Am. J. Physiol.* 255:F800–806.

Reference 36. Kartha, S., Sukhatme, V. P. and Toback, F. G. (1987) *Am. J. Physiol.* 252: F1175–1179.

Reference 37. Kato, Y. et al. (1983) *J. Chromatog.* 447: 212–220.

Reference 38. Katz, E. D. and Dong, M. N. (1990) *Biotechniques* 8(5): 546–554.

Reference 39. Kayano, T., Burant, C. F., Fukumoto, H., Gould, G. W., Fan, Y., Eddy, R. L., Byers, M. G., Shows, T. B., Seino, S., Bell, G. I. (1990) *J. Biol. Chem.* 265:13276–13282.

Reference 40. Klahr, S., Schreiner, G., Ichikawa, I. (1988) *N. Engl. J. Med.* 318:1657–1666.

Reference 41. Klein, J. (1982) *Immunology: The Science of Self-Nonself Discrimination*, John Wiley and Sons, N.Y.

Reference 42. Kujubu, D. A., Fine, L. G. (1989) *Am. J. Kidney Dis.* 14:61–73.

Reference 43. Lachmann, P. J., Strangeways, L., Vyakarnam, A., Evan, G. (1986) *Ciba Foundation Symposium* 119:25–27.

Reference 44. Lathe, R. (1985) *J. Mol. Biol.* 183:1–12.

Reference 45. Lee, C. C., Wu, X., Gibbs, R. A., Cook, R. G., Muzny, D. M., Caskey, C. T. (1988) *Science* 239:1288–1291.

Reference 46. Leighton, J., Brada, Z., Estes, L. W., Justh G. (1969) *Science* 163:472–473.

Reference 47. Manley, J. L. (1984) *Transcription and Translation: A Practical Approach*, p. 71–88.

Reference 48. Martin, B. M., Gimbrone, M. A., Jr., Majeau, G. R., Unanue, E. R., Cotran R. S. (1983) *Am. J. Pathol.* 111:367–373.

Reference 49. McCreary, V., Kartha, S., Bell, G. I. and Toback, F. G. (1988) *Biochemical and Biophysical Communications* 152:862–866.

Reference 50. Mellman, I., Galloway, C. J. (1983) *Meth. Enzymol.* 98:545–555.

Reference 51. Mendley, S. R., Toback, F. G. (1989) *Annu. Rev. Physiol.* 51:33–50.

Reference 52. Mendley, S. R. and Toback, F. G. (1990) *Am. J. Kidney Dis.* 16: 80–84.

Reference 53. Mitchell, W. M. (1977) *Meth. Enzymol.* 47:165–170.

Reference 54. Moench, T. R., Gendelman, H. E., Clements, J. E., Narayan, O., Griffin, D. E. (1985) *J. Virol. Meth.* 21:119–130.

Reference 55. Moolenaar, W. H., Mummery, C. L., von der Soog, P. T. et al. (1981) *Cell* 23: 789–798.

Reference 56. Mordan, L. J., Toback, F. G. (1984) *Am. J. Physiol.* 246:C351–C354.

Reference 57. Nakai, A., Seino, S., Sakurai, A., Szilak, I., Bell, G. I., DeGroot, L. J. (1988) *Proc. Natl. Acad. Sci. U.S.A.* 85:2781–2785.

Reference 58. Nakai, A., Kartha, S., Sakurai, A., Toback, F. G. and DeGroot, L. J. (1990) *Molec. Endocrinol.* 4: 1438–1443.

Reference 59. "National Kidney and Urologic Diseases Advisory Board 1990 Long-Range Plan," U.S. Dept. of Health and Human Services, Public Health Service, National Institutes of Health.

Reference 60. Ohashi, A., Gibson, J., Gregor, I., Schatz, G. (1982) *J. Biol. Chem.* 257:13042–13047.

Reference 61. Pannel, R., Kartha, S., Pogell, B. M. (1980) *Fed. Proc.* 39:3051A.

Reference 62. Parnes, J. R., Velan, B., Felsenfeld, A., Ramanathan, L., Ferrini, U., Appella, E., Seidman, J. F. (1981) *Proc. Natl. Acad. Sci. U.S.A.* 78:2253–2257.

Reference 63. Rabito, C. A., Tchao, R., Valentich, J. Leighton (1980) *In Vitro* 16:461–468.

Reference 64. Rinderknecht, E., Humbel, R. E. (1978) *J. Biol. Chem.* 253:2769–2776.

Reference 65. Rinderknecht, E., Humbel, R. E. (1978) *FEBS Lett* 89:283–286.

Reference 66. Rindler, M. J., Taub, M., Saier, M. H., Jr. (1979) *J. Biol. Chem.* 254:11431–11439.

Reference 67. Risau, W., Ekblom, P. (1986) *J. Cell Biol.* 103:1101–1107.

Reference 68. Roberts, A. D., Anzano, M. A., Meyers, C. A., Wideman, J., Blacher, R., Pan, Y-CE, Stein, S., Lehrman, S. R., Smith, J. M., Lamb, L. C., Sporn, M. B. (1983) *Biochemistry* 22:5692–5698.

Reference 69. Roberts, A. B., Anzano, M. A., Lamb, L. C., Smith, J. M., Sporn, M. B. (1981) *Proc. Natl. Acad. Sci. U.S.A.* 78:5339–5343.

Reference 70. Rollason, H. D. (1949) *Anat. Rec.* 104:263–285.

Reference 71. Roth, J. (1983) *Techniques in Immunocytochemistry* 5 2:217–284.

Reference 72. Sanger, F., Nicklen, S., Coulson, A. R. (1977) *Proc. Natl. Acad. Sci. U.S.A.* 74:5463–5471.

Reference 73. Savage, C. R., Jr., Hash, J. H., Cohen, S. (1973) *J. Biol. Chem.* 248:7669–7672.

Reference 74. Schuldiner, S., Rozengurt, E. (1982) *Proc. Natl. Acad. Sci. U.S.A.* 70:7778–7782.

Reference 75. Segarini, P. R., Roberts, A. B., Rosen, D. M., Seyedin, S.M. (1987) *J. Biol. Chem.* 262:14655–14662.

Reference 76. Silver, B. J., Jaffer, F. E., Abboud, H. E. (1989) *Proc. Natl. Acad. Sci. U.S.A.* 86:1056–60.

Reference 77. Smith, J. B., Rozengurt, E. (1978) *Proc. Natl. Acad. Sci. U.S.A.* 75:5560–5564.

Reference 78. Sporn, M. B. and Roberts, A. B. (1985) *Nature* 313:745–747.

Reference 79. Sporn, M. B., Todaro, G. J. (1980) *N. Engl. J. Med.* 303:878–880.

Reference 80. Stoker, M. G. et al. (1971) *J. Cell. Physiol.* 78:345–354.

Reference 81. Sukhatme, V.P., Kartha, S., Toback, F. G., Taub, R. J., Hoover, R. G. and Tsai-Morris C. H. (1987) *Oncogene Research* 1:343–355.

Reference 82. Szostak, J. W., Stiles, J. I., Tye, B. K., Chiu, P., Sherman, F., Wu, R. (1979) *Meth. Enzymol.* 68:419–428.

Reference 83. Taylor, C. M., Weiss, J. B. (1985) *Biochem. Biophys. Res. Commun.* 133: 911–916.

Reference 84. Thomas, K. A. (1987) *Meth. Enzymol.* 147:120–135.

Reference 85. Toback, F. G., Walsh-Reitz, M. M. and Kartha, S. (1990) *Nordisk Insulin Symposium* 4, p. 185–198.

Reference 86. Toback, F. G. (1977) *Kidney International* 12: 193–198.

Reference 87. Toback, F. G. Havener, J. J., Dodd, R. C. and Spargo, B. H. (1977) *Am. J. Physiol.* 232: E216–222.

Reference 88. Toback, F. G. (1980) *Proc. Natl. Acad. Sci. U.S.A.* 77:6654–6656.

Reference 89. Toback, F. G., Walsh-Reitz, M. M., Mendley, S. R. and Kartha, S. (1990) *Pediatric Nephrology* 4:363–371.

Reference 90. Tucker, R. F., Shipley, G. D., Moses, H. L., Holley, R. W. (1984) *Science* 226:705–707. Nat. Center Health Stat. 1985.

Reference 91. Vlodavsky, I., Folkman, J., Sullivan, R., Fridman, R., Ishai-Michaeli, R., Sasse, J., Klagsbrun, M. (1987) *Proc. Natl. Acad. Sci. U.S.A.* 84:2292–2296.

Reference 92. Waack, S., Walsh-Reitz, M. M., Toback, F. G., (1985) *Am. J. Physiol.* 249:C105–C110.

Reference 93. Walsh-Reitz, M. M., Aithal, H. N., Toback, F. G. (1984) *Am. J. Physiol.* 247:C321–C326.

Reference 94. Walsh-Reitz, M. M., Feldman, R. and Toback, F. G. (1988) *American Journal of Physiology* 254: F747–753.

Reference 95. Walsh-Reitz, M. M., Toback, F. G. (1983) *Am. J. Physiol.* 244:C429–C432.

Reference 96. Walsh-Reitz, M. M., Toback, F. G. (1983); *Am. J. Physiol.* 245:C365–C370.

Reference 97. Walsh-Reitz, M. M., Gluck, S. L., Waack, S., Toback, F. G. (1986) *Proc. Natl. Acad. Sci. U.S.A.* 83:4764–4768.

Reference 98. Walsh-Reitz, M. M., Toback, F. G., Holley, R. W. (1984) *Proc. Natl. Acad. Sci. U.S.A.* 81:793–796.

Reference 99. Watson, C. J., Jackson, J. F. (1984) *DNA Cloning: A Practical Approach* I:79–88.

Reference 100. Weber, M. J., Evans, P. K., Johnson, M. A., McNair, T. F., Nakamura, K. D., Salter, D. W. (1984) *Fed. Proc.* 43:107–112.

Reference 101. Welshons, W. V., Wolf, M. F., Murphy, C. S., Jordan, V. C. (1988) *Molec. Cellular Endocrinol.* 57:169–178.

Reference 102. Wilkinson, J. M. (1986) *Practical Protein Chemistry—A Handbook* 122–148.

Reference 103. Young, R. A., Davis, R. W. (1983) *Proc. Natl. Acad. Sci. U.S.A.* 80:1194–1198.

What is claimed is:

1. A purified and isolated autocrine growth factor which effects growth of kidney epithelial cells and has the following characteristics:

(a) an apparent molecular weight of between 3,500 and 10,000 daltons as determined by SDS polyacrylamide gel electrophoresis and ultrafiltration;

(b) resistant to inhibition by:

(i) 65 mM dithiothreitol (DTT) for at least one hour;

(ii) freezing for one week; or (iii) heating at 56° C. for thirty minutes;

(c) inhibited by:

(i) heating at 100° C. for fifteen minutes;

(ii) exposure to 0.1% trifluoroacetic acid for one hour; or (iii) treatment with 100 μg/ml of trypsin for three hours at 37° C.;

(d) stable in 1% acetic acid and over a pH range from 3.1 to 9.5; and (e) obtained from BSC-1 or MDCK cells or from cells which produce the autocrine growth factor having the characteristics of a factor obtained from BSC-1 or MDCK cells.

* * * * *